United States Patent [19]

Margolius

[11] Patent Number: 6,071,710
[45] Date of Patent: Jun. 6, 2000

[54] ANTIKININ COMPOUNDS AND USES THEREOF

[75] Inventor: Harry S. Margolius, Mt. Pleasant, S.C.

[73] Assignee: MUSC Foundation for Research Development, Charleston, S.C.

[21] Appl. No.: 08/974,735

[22] Filed: Nov. 19, 1997

Related U.S. Application Data

[60] Provisional application No. 60/031,285, Nov. 20, 1996, and provisional application No. 60/064,792, Nov. 10, 1997.
[51] Int. Cl.[7] ............................. G01N 33/53; C07K 5/00; C07K 14/00
[52] U.S. Cl. ........................................... 435/7.21; 435/7.1
[58] Field of Search .................................... 435/7.21, 7.1; 530/300, 350

[56] References Cited

U.S. PATENT DOCUMENTS 5,385,899   1/1995   Kyle et al. ................................ 514/15
5,834,431   10/1998  Stewart et al. ........................... 514/15

FOREIGN PATENT DOCUMENTS 0 524 722   1/1973   European Pat. Off. ...... C07D 207/44

OTHER PUBLICATIONS

Liebmann, C. et al., Descrimination Between Putative Bradykinin B2 Receptor and Subtypes in Guinea Pig Ileum Smooth Iodinable Bradykinin Analog, *Molecular Pharmacology*, 46:949–956, 1994.

De Vries J.G., et al., Construction of a Physiologically Active Photaffinity Probe Based on the Structure of Bradykinin, *Journal of Neurochemistry* 52:5:1508–1516, 1989.

Suzuki, Jenji & Abiko, Takashi, Syntheis of Every Kind of Peptide Fragments of Bradykinin, *Chem. Pharm. Bull.* 17:8:1671–1678, 1969.

Stahl, K.W., Purification and Gel Filtration Chromatography (GFC) of an Antiinflammatory and Macrophogotoxic Peptide from Murine Malignant Cells, *Proc. Eures Symp. Macrophage Cancer* 271–280, 1977.

Miller, L.J., et al., Preparation and Characterization of a Probe for the Cholecystokinin Octrapeptide Receptor, $N^\alpha(^{125}I\text{–desaminotyrosyl})$ CCK–8, and its Interactions with Pancreatic Acini, *J. Biol. Chemistry,* 256:23:12417–12423, 1981.

Hasan, A.A.K., Amenta, S. and Schmaier, A.H., "Bradykinin and its metabolite, Arg–Pro–Pro–Gly–Phe are selective inhibitors of α–thrombin–induced platelet activation", *Circulation* 94:517–528, 1996.

Majima, M., Sunahara, N., Harada, Y., and Katori, M.: "Detection of the degradation products of bradykinin by enzyme immunoassays as markers for the release of kinin in vivo" *Biochem. Pharmacol.* 45:559–567, 1993.

Shima, C., Majima, M., and Katori, M., "A stable metabolite, Arg–Pro–Pro–Gly–Phe, of bradykinin in the degradation pathway in human plasma", *Japan J. Pharmacol.* 60:111–119, 1992.

08/,675,821 01/1999 Rosazza et al. 435 191.

*Primary Examiner*—Elizabeth Kemmerer
*Assistant Examiner*—Nirmal S. Basi
*Attorney, Agent, or Firm*—Needle & Rosenberg, P.C.

[57] ABSTRACT

An analog of the peptide consisting of RPPGF (SEQ ID N0:1) is provided. Mimetics of RPPGF (SEQ ID NO:1) and its retropeptide, FGPPR, are also provided. A peptide is provided having an antikinin activity and having the sequence $X_1$-R-P-P-G-F-$X_2$ (SEQ ID NO:5), $X_1$-F-G-P-P-R-$X_2$ (SEQ ID NO:7). Provided are methods of screening for a mimetic or analog of RPPGF (SEQ ID NO:1) or FGPPR (SEQ ID NO:2), screening for an RPPGF (SEQ ID NO:1) receptor, or screening for an antagonist of RPPGF (SEQ ID NO:1) or FGPPR (SEQ ID NO:2) is provided. Methods of treating conditions that can be treated by an antikinin activity and diseases that are associated with an antikinin activy are also provided.

11 Claims, 12 Drawing Sheets

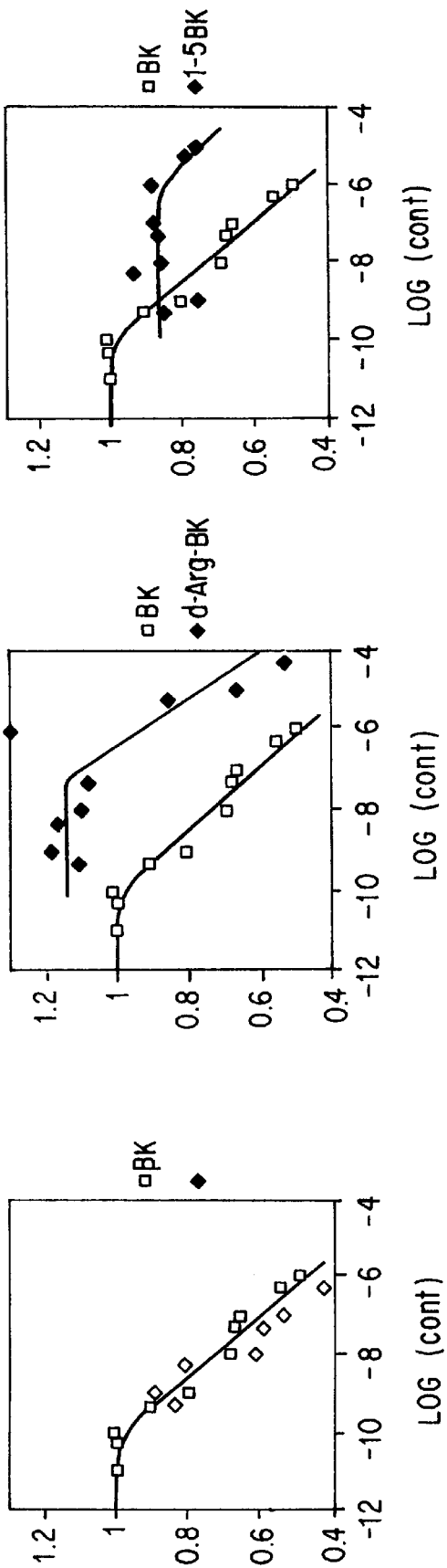

ANTIKININ COMPOUNDS AND USES THEREOF

This is a continuation-in-part of provisional application Ser. No. 60/031,285 filed Nov. 20, 1996 and continuation-in-part of provisional application Ser. No. 60/064,792, filed Nov. 10, 1997.

BACKGROUND OF THE INVENTION

1. Field of the Invention

The invention relates, generally, to antikinin compounds, and specifically to uses of the pentapeptide, Arg-Pro-Pro-Gly-Phe (RPPGF)(SEQ ID NO:1). More specifically, the invention relates to the use of RPPGF (SEQ ID NO:1) to screen for an RPPGF (SEQ ID NO:1) receptor and for antagonists and mimetics of RPPGF. The invention also relates to the use of RPPGF (SEQ ID NO:1) to treat diseases.

2. Background Art

All animal life regulates the internal biological environment via hormonal systems. These often consist of gene product-protein substrates synthesized in depots (such as the liver, or specific endocrine organs), and highly specific proteolytic enzymes called either proteases or proteinases, which attack specific peptide bonds in the substrates to cleave out smaller, generally very potent peptide hormones of various length and sequence. After these peptide hormones bind to their specific receptors, usually expressed upon the surface of target cells in target tissues, and induce signal transduction to ultimately cause some biological response, the hormones are metabolized by enzymes called peptidases, which are more generally non-specific and, thus, capable of cleaving multiple peptide hormones to smaller, generally inactive peptide fragments.

Two, unusually interlocking, substrate-protease-peptide hormone-peptidase systems are the renin-angiotensin system. The protein antigotensinogen (also called renin substrate) is made in the liver, attacked in the blood by the specific protease called renin, synthesized, stored and released from the kidney, to cleave out angiotensin I, a decapeptide with surprisingly little biological activity. However, after removal of its' C-terminal histidine, leucine by a second enzyme called angiotensin I-converting enzyme (ACE), which is enriched on the surface of pulmonary vascular endothelial cells, the octapeptide angiotensin II is formed, an extremely potent vasoconstrictor and, thus, a regulator of vascular resistance (blood pressure) and other physiologic processes.

More than twenty years ago, the first potent synthetic inhibitors of angiotensin I-converting enzyme, based upon an unusual, natural pentapeptide inhibitor of the enzyme found in the venom of the South American viper, *Bothrops jararaca*, were reported (1). These inhibitors (the so-called, "ACE" inhibitors), are now amongst the world's most widely used antihypertensive drugs.

From the outset of work on the natural (or subsequent synthetic) inhibitors of ACE (angiotensin converting enzyme), it was known that this enzyme is bifunctional, that is, it has two natural substrates, and in fact, its' preferred substrate is not angiotensin I, but rather the deca- or non-apeptide hormones called lysyl-bradykinin (kallidin) or bradykinin (2). For this reason, the same enzyme is also called kininase II (there are several other peptidases for kinins including a kininase I). However, rather than forming an active hormone in this role, ACE/kininase II catabolizes the kinins by sequentially removing two dipeptides from the C-terminal end to fragments which have uniformly been considered to be inactive degradation products of the kinin peptides (2). Because the kinin peptides are amongst the most powerful vasodilator (hypotensive) peptides known, there is increasing consideration of the possible roles of kinins in blood pressure control (3). In addition, and finally there are recent discoveries suggesting that fragments of some peptide hormones, widely considered to be inactive, are capable of producing biological responses (4–6).

Bradykinin (BK) is the cleavage product of the action of the enzyme tissue kallikrein upon the substrate, low molecular weight kininogen. The plasma half-life of the generated BK is short ($t_{1/2}$~15 secs.). The degradation of BK is the result of proteolytic cleavages produced by the enzymes kininase II (ACE) and other peptidases such as kininase I and neutral endopeptidase 24.11. The initial digestion of BK by kininase II results in the removal of the terminal phenylalanine-arginine, leaving the heptapeptide des-Arg9-Phe8-BK. Subsequent cleavage of des-Arg9-Phe8-BK results in additional BK fragmented peptides, including the pentapeptide BK1-5. These degradation peptides of BK, including BK1-5, have been considered for decades to be inactive.

The generation and degradation of BK occurs during episodes of tissue damage, allergic reactions and inflammatory responses. BK has been shown to mediate the body's responses to these events. BK's principal cardiovascular effect is one of vasodilation. In fact, BK has been shown to be a mediator in the pathological hypotension associated with septic (endotoxin) shock. Conversely, prolongation of the half-life of BK by ACE inhibitors may contribute to the beneficial actions of these drugs (3). Thus, BK is now considered to be important to cardiovascular responsiveness to homeostatic perturbations.

There is no prior art considering the possibility that kinin fragments have any counter regulatory influence to modulate the actions of the parent kinins.

Determining if endogenous metabolites of BK have any previously undetected role in homeostatic responses to perturbations or disease would allow for the development of stable mimetics of this metabolite as therapeutic agents. Development of such mimetics would be useful for treatment of pathological conditions in which BK has been shown to be detrimental, such as endotoxin shock.

The present invention provides the surprising discovery that RPPGF (SEQ ID NO:1) has many pharmacologic activities that are opposed to the activity of bradykinin.

BRIEF DESCRIPTION OF THE FIGURES

FIG. 7A shows the specific binding of bradykinin to kinin $B_2$ receptors in rat aortic smooth muscle cells. The binding of the parent kinin is specifically displaced by HOE140 (icatibant), a specific kinin $B_2$ receptor antagonist.

FIG. 7B shows the specific binding of bradykinin to kinin $B_2$ receptors in rat aortic smooth muscle cells. The specific binding of bradykinin is not displaced by des-arg9-bradykinin, a $B_1$ receptor antagonist, showing that the binding of the parent bradykinin is specific to its $B_2$ receptors.

FIG. 7C shows the specific binding of bradykinin to kinin $B_2$ receptors in rat aortic smooth muscle cells. The specific binding of bradykinin is not effected by RPPGF, indicating that the results in FIG. 6 are not mediated by a known receptor and occur via some new, potentially unique mechanism.

Thus, in these studies, both (l)- and (d)-BK1-5 protected isolated aortic segments against the deleterious effects of LPS.

Figure 12A:
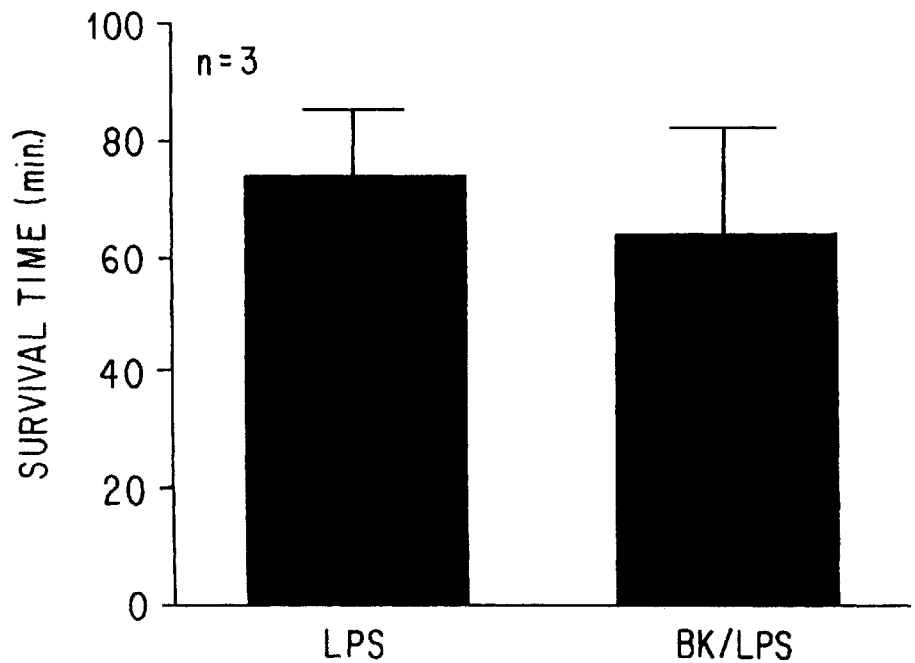
Figure 12B:
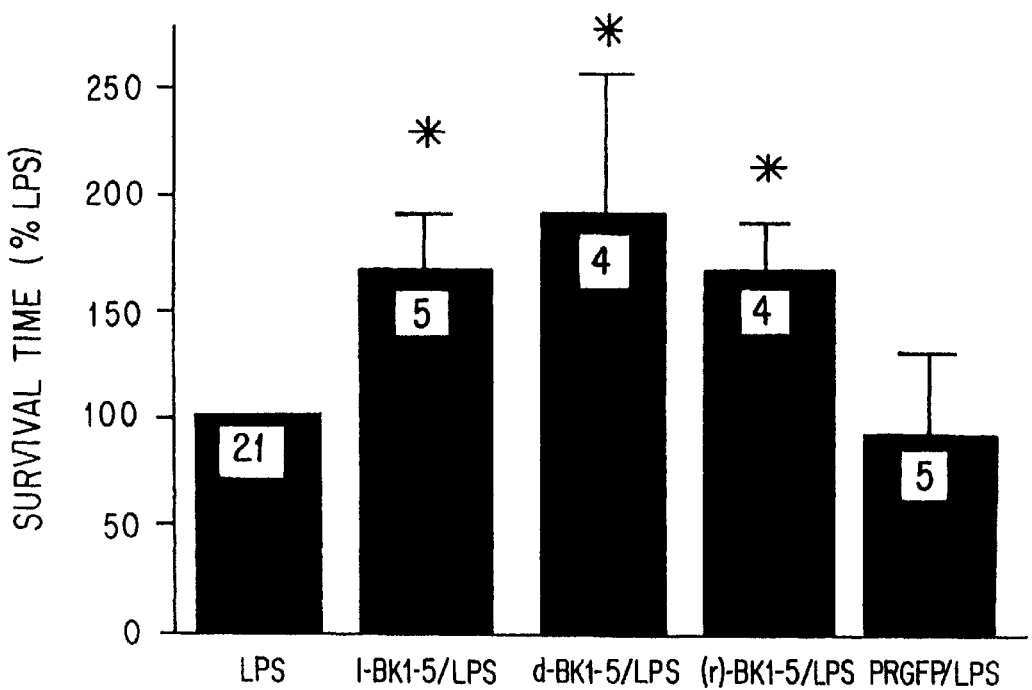

FIGS. 12A–12B show the effect of Bradykinin, RPPGF (SEQ ID NO:1) (BK1-5) and its analogs on survival time of endotoxin (LPS)-treated anesthetized rats. Lipopolysaccharide (LPS) treatment of rats in an accepted model of endotoxic shock. Bradykinin (BK) and its stable fragment (1) BK1-5 as well as (d)BK1-5, (retro)BK1-5(i.e. FGPPR (SEQ ID NO:2)) and scrambled BK1-5, (i.e. PRGFP (SEQ ID NO:15)) were tested for their ability to prolong survival time in this model. Anesthetized male Sprague-Dawley rats were given vehicle, BK or the BK1-5 cogener (1 µg/kg IV followed by 143 ng/kg/hr) for one hour prior to administration of LPS (12 mg/kg IV). In the BK studies, the kininase II inhibitor captopril (1 mg/kg) was given 15 minutes prior to BK or vehicle. Rats were monitored for changes in blood pressure and heart rate subsequent to the administration of LPS. A) Results from the bradykinin (BK) studies; B) Results from the BK1-5 studies. Survival time was compared to that seen for animals treated with vehicle/LPS. Values are the means ± sem from indicated number of animals. *p<0.05 vs. vehicle/LPS. This data shows that pre-treatment of rats with bradykinin does not provide protection, while BK1-5 does provide protection against endotoxin.

Figure 13:
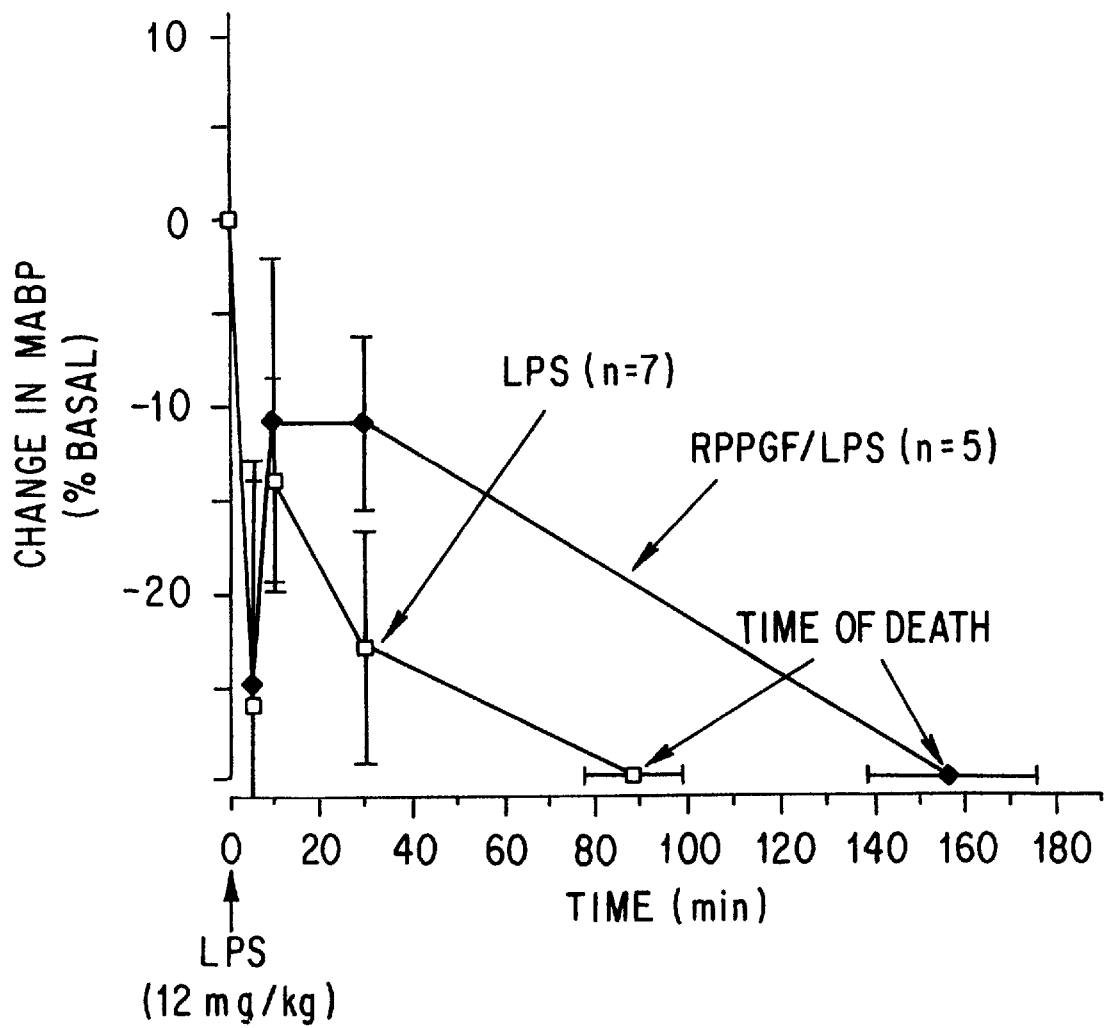

FIG. 13 shows the time course of changes in blood pressure in endotoxin (LPS) treated rats. As in FIG. 12, rats were treated with BK1-5 or saline, followed by administration of LPS. Blood pressure was monitored with time and changes were related to pre-LPS levels.

Figure 14:
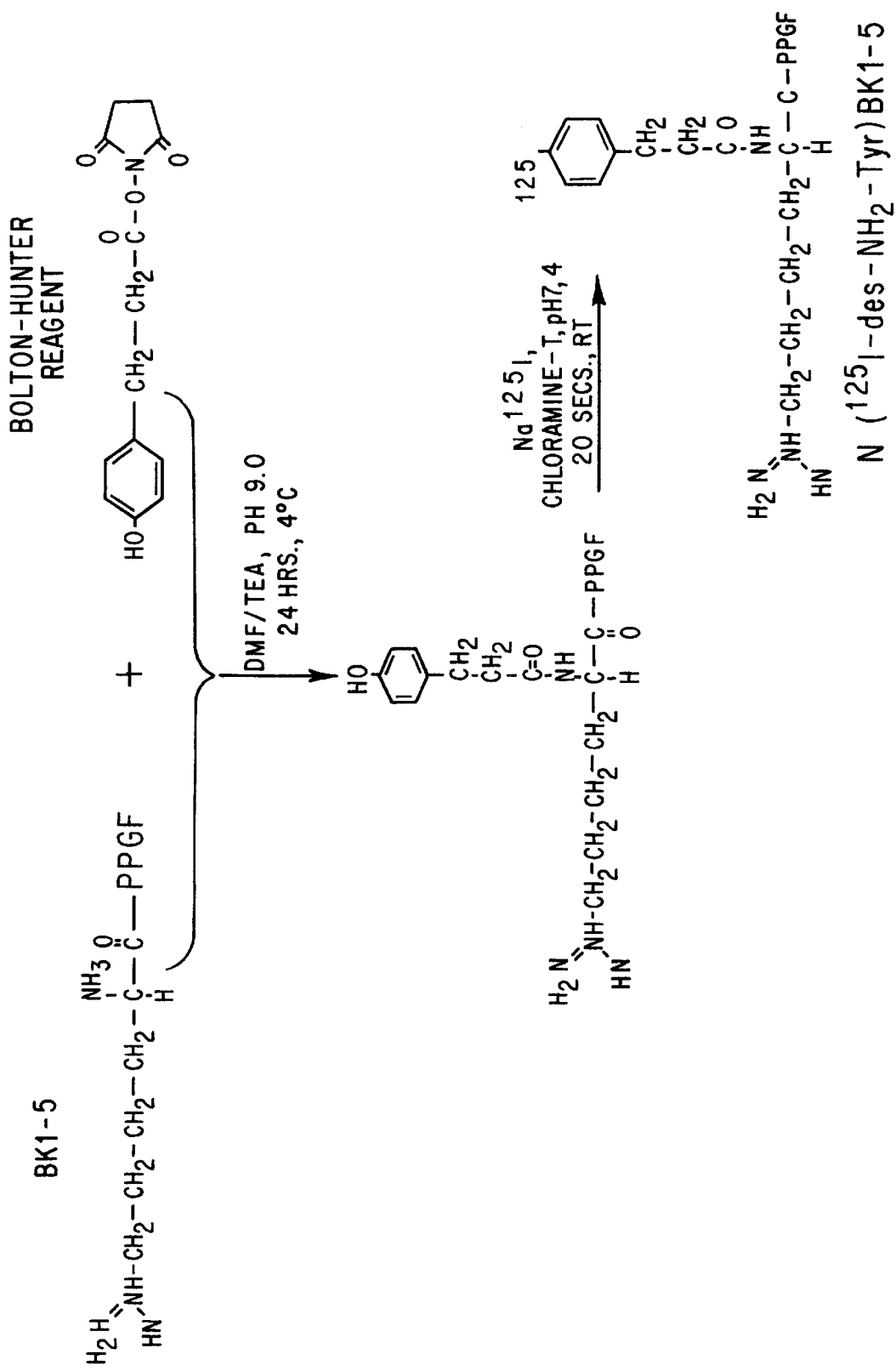

FIG. 14 shows the synthesis of radioiodinated RPPGF (BK1-5). BK1-5 was treated with commercially available Bolton-Hunter reagent under the indicated conditions. The product was purified by HPLC (C18 column with a gradient of 0–90% Acetonitrile in 0.1% TFA). This intermediary 930% conversion from BK1-5) was characterized by MALDI mass spectrometry. Radioiodination was performed by standard chloramide-T procedures and after purification by HPLC, yielded 5% incorporation of $^{125}$I into the final product.

SUMMARY OF THE INVENTION

An analog of the peptide consisting of RPPGF (SEQ ID NO:1) is provided. Mimetics of RPPGF (SEQ ID NO:1) and its retropeptide, FGPPR (SEQ ID NO:2), are also provided.

A peptide is provided having an antikinin activity and having the sequence $X_1$-R-P-P-G-F-$X_2$ (SEQ ID NO:5), wherein $X_1$ and $X_2$ are zero or one or more amino acids which do not destroy the antikinin activity and wherein at least one of the amino acids selected from RPPGF (SEQ ID NO:1) is a (d) amino acid.

An isolated peptide consisting of all (d)RPPGF is provided. An isolated peptide $N^{-\alpha}$ ($^{125}$I-desNH$_2$-Tyr)BK1-5 is provided. A peptide is provided having an antikinin activity having the sequence $X_1$-P-P-G-F-$X_2$ (SEQ ID NO:6), wherein $X_1$ and $X_2$ can be zero or one or more amino acids which do not destroy the antikinin activity.

A peptide is provided having an antikinin activity and the sequence $X_1$-F-G-P-P-R-$X_2$ (SEQ ID NO:7), wherein $X_1$ and $X_2$ can be zero or one or more amino acids which do not destroy the antikinin activity.

Also provided a is method of screening for a mimetic or analog of RPPGF (SEQ ID NO:1) or FGPPR (SEQ ID NO:2) comprising the steps of a) contacting a model system known to express an activity of RPPGF (SEQ ID NO:1) or FGPPR (SEQ ID NO:2) in the presence of RPPGF (SEQ ID NO:1) or FGPPR (SEQ ID NO:2) with a putative agonist analog; b) detecting the presence or absence of the known activity of RPPGF (SEQ ID NO:1) or FGPPR (SEQ ID NO:2) in the presence of the putative mimetic; and c) correlating the presence or absence of the activity with the presence of a mimetic of RPPGF (SEQ ID NO:1) or FGPPR (SEQ ID NO:2).

The invention also provides a method of screening for an RPPGF receptor comprising the steps of a) contacting a cell, cellular components, or tissue with RPPGF (SEQ ID NO:1) or an analog thereof; b) detecting the presence of binding of the RPPGF (SEQ ID NO:1) or analog to the tissue; and c) correlating the presence of binding with the presence of a receptor for RPPGF (SEQ ID NO:1). For example, this method can comprise the steps of a) contacting a tissue with $^{125}$I-tyrosine0-BK1-5, $N^{\alpha}$($^{125}$I-desNH$_2$-Tyr)-RPPGF (SEQ ID NO:1) or RPPGF-$^{125}$I (SEQ ID NO:1); b) detecting the presence of binding of the $^{125}$I-tyrosine0-BK1-5, $N^{\alpha}$($^{125}$I-desNH$_2$-Tyr)-RPPGF (SEQ ID NO:1) or RPPGF-I$^{125}$ (SEQ ID NO:1) to the tissue; and c) correlating the presence of binding with the presence of a receptor for RPPGF. This method can further comprise isolating the receptor from the cell, cellular components, or tissue.

Thus, a method of screening for an antagonist of RPPGF (SEQ ID NO:1) or FGPPR (SEQ ID NO:2) is provided, comprising: a) contacting a model system known to express an activity of RPPGF (SEQ ID NO:1) or FGPPR (SEQ ID NO:2) in the presence of RPPGF (SEQ ID NO:1) or FGPPR (SEQ ID NO:2) with a putative antagonist in the presence of RPPGF (SEQ ID NO:1) or FGPPR (SEQ ID NO:2); b) detecting the absence of, or reduction in, the known activity of RPPGF (SEQ ID NO:1) or FGPPR (SEQ ID NO:2) in the presence of the putative antagonist; and c) correlating the absence of, or reduction in, the activity with the presence of an antagonist of RPPGF (SEQ ID NO:1).

Methods of treating conditions that can be treated by an antikinin activity and diseases that are associated with an antikinin activy are also provided.

DETAILED DESCRIPTION OF THE INVENTION

Pentapeptide, Analogs, Mimetics, Agonists and Antagonists

An analog of the peptide consisting of RPPGF (SEQ ID NO:1) is provided. An "analog" is any compound structurally similar to RPPGF (SEQ ID NO:1) which has an antikinin activity of RPPGF (SEQ ID NO:1) (also referred to herein collectively as "the pentapeptide", "BK1-5", or "minkinin"). The compounds of this invention have antikinin activity. "Antikinin activity" is defined as having at least one activity which is not possessed by bradykinin or is contrary to an activity of bradykinin. Numerous examples of antikinin activities are provided herein.

Mimetics of RPPGF (SEQ ID NO:1) and its retropeptide, FGPPR (SEQ ID NO:2), are also provided. Mimetics include, for example, peptides and small molecules which mimic the function of these pentapeptides, although they need not be structurally related.

A peptide is provided having an antikinin activity and having the sequence $X_1$-R-P-P-G-F-$X_2$ (SEQ ID NO:5), wherein $X_1$ and $X_2$ are zero or one or more amino acids which do not destroy the antikinin activity and wherein at least one of the amino acids selected from RPPGF (SEQ ID NO:1) is a (d) amino acid. In this peptide, at least two of the amino acids selected from RPPGF (SEQ ID NO:1)are (d) amino acids. In this peptide, at least three of the amino acids selected from RPPGF (SEQ ID NO:1) are (d) amino acids. In this peptide, at least four of the amino acids selected from RPPGF (SEQ ID NO:1) are (d) amino acids. In this peptide, all five of the amino acids selected from RPPGF (SEQ ID NO:1) are (d) amino acids. In this peptide, $X_1$ can be Lysine, Serine, or Serine-Proline.

An isolated peptide consisting of all (d)RPPGF (SEQ ID NO:1) is provided.

An isolated peptide $N^{-\alpha}$($^{125}$I-desNH$_2$-Tyr)BK1-5 is provided.

A peptide is provided having an antikinin activity having the sequence $X_1$-P-P-G-F-$X_2$ (SEQ ID NO:5) wherein $X_1$ and $X_2$ can be zero or one or more amino acids which do not destroy the antikinin activity. In this peptide, $X_1$ can be zero and $X_2$ is Serine. In this peptide, $X_1$ can be zero and $X_2$ is Serine-Proline. In this peptide, at least one of the amino acids selected from P-P-G-F (SEQ ID NO:8) can be a (d) amino acid. In this peptide, at least two of the amino acids selected from P-P-G-F (SEQ ID NO:8) can be (d) amino acids. In this peptide, at least three of the amino acids selected from P-P-G-F (SEQ ID NO:8) can be (d) amino acids. In this peptide, at all four of the amino acids selected from P-P-G-F (SEQ ID NO:8) can be (d) amino acids.

A peptide is provided having an antikinin activity and the sequence $X_1$-F-G-P-P-R-$X_2$ (SEQ ID NO:7), wherein $X_1$ and $X_2$ can be zero or one or more amino acids which do not destroy the antikinin activity. In this peptide, at least one of the amino acids selected from FGPPR (SEQ ID NO:2) can be a (d) amino acid. In this peptide, at least two of the amino acids selected from FGPPR (SEQ ID NO:2) can be (d) amino acids. In this peptide, at least three of the amino acids selected from FGPPR (SEQ ID NO:2) can be (d) amino acids. In this peptide, at least four of the amino acids selected from FGPPR (SEQ ID NO:2) can be (d) amino acids. In this peptide, all five of the amino acids selected from FGPPR can be (d) amino acids. In this peptide, $X_2$ can be Lysine, $X_1$ can be Serine or $X_1$ can be Proline-Serine.

$X_1$ and $X_2$ as used herein can also be (d) amino acids.

Structurally similar analogs of RPPGF (SEQ ID NO:1) can include substitutions of other amino acids with similar characteristics. For example, histidine can be substituted for arginine as both are basic, hydrophilic residues. A resulting peptide is HPPGF (SEQ ID NO:13). Alanine can be substituted for glycine. Both are hydrophobic, nonpolar aliphatic residues. A resulting peptide is RPPAF (SEQ ID NO:14). Similarly, substitutions with one or more (d)-amino acids can be synthesized.

Examples of (d)-containing RPPGF (SEQ ID NO:1) analogs are as follows:
(d)Arg-(d)Pro-(d)Pro-(d)Gly-(l)Phe (SEQ ID NO:1)
(d)Arg-(d)Pro-(d)Pro-(l)Gly-(d)Phe (SEQ ID NO:8)
(d)Arg-(d)Pro-(l)Pro-(d)Gly-(d)Phe (SEQ ID NO:1)
(d)Arg-(l)Pro-(d)Pro-(d)Gly-(d)Phe (SEQ ID NO:1)
(l)Arg-(d)Pro-(d)Pro-(d)Gly-(d)Phe (SEQ ID NO:1)
(d)Arg-(d)Pro-(d)Pro-(l)Gly-(l)Phe (SEQ ID NO:1)
(l)Arg-(d)Pro-(d)Pro-(l)Gly-(l)Phe (SEQ ID NO:1)
(d)Arg-(d)Pro-(l)Pro-(l)Gly-(l)Phe (SEQ ID NO:1)
(l)Arg-(l)Pro-(d)Pro-(l)Gly-(l)Phe (SEQ ID NO:1)
(d)Arg-(l)Pro-(l)Pro-(l)Gly-(l)Phe (SEQ ID NO:1)
(l)Arg-(l)Pro-(l)Pro-(l)Gly-(l)Phe (SEQ ID NO:1)
(l)Arg-(d)Pro-(d)Pro-(d)Gly-(d)Phe (SEQ ID NO:1)
(l)Arg-(d)Pro-(d)-Pro-(d)-Gly-(l)-Phe (SEQ ID NO:1)
(l)Arg-(l)Pro-(d)-Pro-(d)-Gly-(l)-Phe (SEQ ID NO:1)
(l)Arg-(l)Pro-(l)-Pro-(d)-Gly-(l)-Phe (SEQ ID NO:1)
(d)Arg-(l)Pro-(l)Pro-(d)Gly-(d)Phe (SEQ ID NO:1)
(d)Arg-(l)Pro-(d)-Pro-(l)-Gly-(d)-Phe (SEQ ID NO:1)
(l)Arg-(d)Pro-(l)-Pro-(l)-Gly-(d)-Phe (SEQ ID NO:1)
(l)Arg-(l)Pro-(d)-Pro-(l)-Gly-(d)-Phe (SEQ ID NO:1)
(l)Arg-(l)Pro-(d)-Pro-(d)-Gly-(d)-Phe (SEQ ID NO:1)
(l)Arg-(l) Pro-(l)-Pro-(d)-Gly-(d)-Phe (SEQ ID NO:1)
(l)Arg-(l)Pro-(l)-Pro-(l)-Gly-(d)-Phe (SEQ ID NO:1)

The retropeptide with similar (d) amino acid substitutions is also provided.

Modifications could also be made to the peptide termini such as acetylations. Amino acids can be added to the termini of RPPGF (SEQ ID NO:1), so long as they do not alter the activity of the peptide. For example, RPPGFSP (SEQ ID NO:6) (BK1-7), PPGRSP (SEQ ID NO:9) (BK2-7) and lys-RPPGF (SEQ ID NO:10) (a fragment of Lys-Bradykinin) can be made and tested in the assays described below and used in the methods described below using RPPGF (SEQ ID NO:1). Addition of an n-terminal tyrosine, or conjugation with Bolton-Hunter reagent, or tri-methyl tin substitution on the C-terminal phenylalanine would allow any synthesized peptides to be radioiodinated and used in receptor characterization studies and in quantitation of RPPGF or its analogs in biological fluids.

A series of such analogs can be routinely synthesized and subjected to structure-function studies. The modified peptides can be tested for antikinin activity. They can also be used to evaluate the importance of individual amino acid positions.

Even smaller fragments of bradykinin can have biological activity. It is well known that RPP (SEQ ID NO:11) (BK1-3) is a kinin end product of an enzyme called post-proline cleaving enzyme in the mammalian kidney. This tripeptide can have pharmacologic activity at its cellular sites of production, most notably along the proximal portions of the nephron where post-proline cleaving enzyme is localized. Thus, RPPGF (SEQ ID NO:1) can demonstrate actions at this location that are limited by catabolism to the tripeptide. Such actions include diuresis and natriuresis, that is, water and salt loss and efficacy in diseases of their retention, such as heart failure or hypertension. Thus, the invention provides $X_1$-RPP-$X_2$ (SEQ ID NO:12), wherein $X_1$ can be zero or one or more amino acids that retains an antikinin activity. One or more of the amino acids can be a (d) amino acid.

A specific example of an isolated analog of RPPGF (SEQ ID NO:1) consists of the retrominikinin, FGPPR (SEQ ID NO:2). Further examples include the (d) amino acid forms or RPPGF (SEQ ID NO:1) and FGPPR (SEQ ID NO:2), as well as HPPGF (SEQ ID NO:13), RPPAF (SEQ ID NO:14), $N^{\alpha}$($^{125}$I-desNH$_2$-Tyr)-RPPGF (SEQ ID NO:1), $^{125}$I-tyrosine0-Bk1-5 and $^{125}$I-RPPGF. In addition, one would synthesize compounds that share some structural characteristic with RPPGF (SEQ ID NO:1) by methods standard in the art. These peptides can be synthesized, for example, using solid-phase synthesis and standard F-MOC chemistry. Then one would screen the compound in the methods set out below.

Alternatively, peptide display libraries could be designed and screened for activity as described below or screened for binding to the RPPGF receptor. The use of random peptide phage libraries to isolate compounds for target proteins has yielded a variety of peptides that recognize specific target proteins with interesting biological activities. Such a strategy has provided interesting binding peptides which recognize important proteins including antibodies (40, 41, 42, 43), streptavidin (44), calmodulin (45), SH3 domain (46), and endoplasmic reticulum protein BiP (47). Some of these peptides have yielded important insights into the structure-function of the target protein. For example, analysis of peptides that bind to BiP have shown that BiP preferentially binds peptides containing a subset of aromatic and hydrophobic amino acids in alternating positions, suggesting that peptides bind in an extended conformation, with the side chains of alternating residues pointing into a cleft on the BiP molecule (47).

Alternatively, differential display can be utilized to quickly find small molecule analogs or antagonists of RPPGF (SEQ ID NO:1) (8).

Also provided a is method of screening for a mimetic or analog of RPPGF (SEQ ID NO:1) or FGPPR (SEQ ID NO:2) comprising the steps of a) contacting a model system known to express an activity of RPPGF (SEQ ID NO:1) or FGPPR (SEQ ID NO:2) in the presence of RPPGF (SEQ ID NO:1) or FGPPR (SEQ ID NO:2) with a putative agonist analog; b) detecting the presence or absence of the known activity of RPPGF (SEQ ID NO:1) or FGPPR (SEQ ID NO:2) in the presence of the putative mimetic; and c) correlating the presence or absence of the activity with the presence of a mimetic of RPPGF (SEQ ID NO:1) or FGPPR (SEQ ID NO:2).

In the method of screening for a mimetic of RPPGF (SEQ ID NO:1), the activity can be an antikinin activity, an activity associated with hypotension, an activity associated with endotoxemia secondary to bacterial sepsis, an activity associated with an inflammatory condition, an activity associated with pain, an activity associated with osteoclastic activity, an activity associated with electrolyte and water excretion, an activity associated with oscillations in the level of free intracellular calcium, an activity associated with DNA synthesis, an activity associated with tyrosyl phosphorylation of cytoplasmic proteins, an activity associated with prostaglandin synthesis, an activity associated with cyclooxygenase products, or an activity associated with inhibition of inducible nitric oxide.

To identify potential mimetics of the RPPGF (SEQ ID NO:1) or FGPPR (SEQ ID NO:2) and its analogs, pharmacological screening assays are performed. These are performed in several model screening systems, such as, but not limited to, intracellular calcium measurements, platelet aggregation studies, c-AMP assays, rodent aortic ring contraction, epithelial transport, uterine contraction, cyclooxygenase-1, cyclooxygenase-2 and nitric oxide (iNOS, cNOS, eNOS) activity assays. Initial screening can include known bradykinin fragments and analogs, as well as known agonists to the parent kinins.

The analog or mimetic of RPPGF (SEQ ID NO:1) can be in a pharmaceutically acceptable carrier. A therapeutically effective amount of the peptide consisting of RPPGF (SEQ ID NO:1), FGPPR (SEQ ID NO:2) or an analog of these pentapeptides is provided. For example, the amount of the pentapeptide or analog thereof can be from about $10^{-9}$ to $10^{-6}$ molar. The amounts showing activity typically range from $10^{-9}$ to $10^{-6}$ molar, depending upon assay systems being used, for example, vascular smooth muscle cells, brain glial cells, etc.

Thus, the invention provides a composition comprising a therapeutically effective amount of the pentapeptide consisting of RPPGF (SEQ ID NO:1), FGPPR (SEQ ID NO:2), analogs, agonists or combinations thereof and a pharmaceutically acceptable carrier. Examples and descriptions of acceptable carriers are described herein and in the literature (see, for example Remington's Pharmaceutical Sciences, latest addition).

RPPGF (SEQ ID NO:1) has a long half-life and, therefore, is particularly suited for injection. When desirable, to prevent degradation and insure delivery to specific targets such as the vascular wall, brain tissue, or the epithelial cells of the kidney nephron, for example, encapsulating the peptide or its analogs within protective molecules, such as liposomes or molecules of fullerenes can allow either for oral administration of the peptide or its analogs, or targeted delivery to specific sites. In addition, pharmaceutically acceptable carriers might include ointments with oil or aqueous bases for topical application to burned skin surfaces, where antikinin analgesic and anti-inflammatory effects would be of therapeutic benefit (see, for example, Remington's Pharmaceutical Sciences, latest edition).

A purified receptor of RPPGF (SEQ ID NO:1) is provided. A "receptor" is defined as a molecule or molecular complex on or within a cell that binds to or interacts with RPPGF. Methods designed to identify one or more receptors for RPPGF and its analogs can employ $^{125}$I-tyrosine0-BK1-5. Radioligand binding assays can then be performed on a wide array of target tissues and cultured cells having receptors including, but not limited to vascular tissue, kidney homogenates, cultured vascular smooth muscle cells, renal tubular epithelial cells, endothelial cells, fibroblasts, platelets, non-platelets, neuronal cells (including glial cells), and skin fibroblasts.

Thus, the invention also provides a method of screening for an RPPGF (SEQ ID NO:1) receptor comprising the steps of a) contacting a cell, cellular components, or tissue with RPPGF (SEQ ID NO:1) or an analog thereof; b) detecting the presence of binding of the RPPGF (SEQ ID NO:1)or analog to the tissue; and c) correlating the presence of binding with the presence of a receptor for RPPGF (SEQ ID NO:1). For example, this method can comprise the steps of a) contacting a tissue with $^{125}$I-tyrosine0-BK1-5, $N^{\alpha}(^{125}$I-desNH$_2$-Tyr)-RPPGF or RPPGF-$^{125}$I; b) detecting the presence of binding of the $^{125}$I-tyrosine0-BK1-5, $N^{\alpha}(^{125}$I-desNH$_2$-Tyr)-RPPGF or RPPGF-I$^{125}$ to the tissue; and c) correlating the presence of binding with the presence of a receptor for RPPGF. This method can further comprise isolating the receptor from the cell, cellular components, or tissue.

A purified antagonist of the activity of the peptide consisting of RPPGF (SEQ ID NO:1) is also provided. An "antagonist" is defined as a compound that binds RPPGF or a compound, including antibodies, that binds the receptor for the RPPGF (SEQ ID NO:1) and prevents an activity of RPPGF (SEQ ID NO:1). Non-antibody antagonists are also provided. Antagonists to the actions of the RPPGF (or its analogs) are also called "antiminikinins". Antibody and non-antibody antagonists can be used in the methods of the invention. Such compounds most likely bind the receptor or other such molecular species (e.g. enzymes) with which the RPPGF or its analogs combine.

Thus, a method of screening for an antagonist of RPPGF (SEQ ID NO:1) or FGPPR (SEQ ID NO:2) is provided, comprising: a) contacting a model system known to express an activity of RPPGF or FGPPR (SEQ ID NO:2) in the presence of RPPGF (SEQ ID NO:1) or FGPPR (SEQ ID NO:2) with a putative antagonist in the presence of RPPGF (SEQ ID NO:1) or FGPPR (SEQ ID NO:2); b) detecting the absence of, or reduction in, the known activity of RPPGF (SEQ ID NO:1) or FGPPR (SEQ ID NO:2) in the presence of the putative antagonist; and c) correlating the absence of, or reduction in, the activity with the presence of an antagonist of RPPGF (SEQ ID NO:1).

In the method of screening for an antagonist, the activity can be an activity associated with diabetes, an activity associated with atherosclerosis, an activity associated with renal failure, an activity associated with stroke, an activity associated with cardiac failure, an activity associated with myocardial infarction, or an activity associated with hypertension.

To identify potential antagonists to the peptide, which can be used therapeutically, pharmacological screening assays are performed. These are performed in several model screening systems, such as, but not limited to, intracellular calcium measurements, platelet aggregation studies, c-AMP assays, rodent aortic ring contraction and others described herein. Initial screening can include known bradykinin fragments and analogs, as well as known antagonists to the parent kinins such as HOE140 (icatibant).

Strategies used to synthesize antagonist candidates are known in the art (9).

An enzyme known as "post-proline cleaving enzyme" (prolyl endopeptidase) is found in high concentrations in brain and kidney, and should efficiently destroy RPPGF by cleavage after P in position 3. Its specific sites of localization (e.g. renal epithelial cells) make it a target for inhibition to confirm either physiologic or pathologic effects attributable to sustaining the life of RPPGF (10). An inhibitor of prolyl endopeptidase, prostatin, is disclosed by Majima et al., *Eur. J. Pharmacol.*, 232:181–190 (1993). Prostatin is val-val-3-amino-2-oxovaleryl-D-leu-val, and can be isolated from Streptomyces.

The invention provides inhibitors of post-proline cleaving enzyme, which prolong the half life of RPPGF. As used herein the term "inhibit" means reducing the synthesis (e.g., by reducing transcription or translation), or the activity (e.g., by interfering with binding, etc.), speeding the degradation of whatever is being inhibited (e.g., RPPGF (SEQ ID NO:1), proyl endopeptidase, etc.) or any combinations of these mechanisms. Thus, the invention also provides a method of inhibiting prolyl endopeptidase activity, by inhibiting its synthesis, interfering with its active sight, etc. As further describe below, this method can be used to treat conditions that can be treated with antikinin activity.

Treatment Methods

The present experimental evidence supports a widespread pharmacological activity of RPPGF (SEQ ID NO:1). Thus, a method of treating a condition in a subject which can be treated by an antikinin activity or inhibition of an antikinin activity is provided. The term "subject" as used herein can be a human or it can be a non-human animal being treated in a veterinary context. The method comprises administering to the subject a therapeutic amount of a compound selected from the group consisting of RPPGF (SEQ ID NO:1), FGPPR (SEQ ID NO:2), analogs or mimetics thereof. The term "condition" includes, for example the cardiovascular, renal and inflammatory diseases described herein as well as circumstances such as thermal burns, or sunburn, in which kinins play a role in the inflammatory response and in pain production. Similarly, treatment can be effected by administering an activator of RPPGF (SEQ ID NO:1) production, so that endogenous RPPGF (SEQ ID NO:1) levels rise. As used herein, the terms "activate," "activation" etc. mean to increase the production (e.g., by increasing transcription or translation), to increase efficiency on a molecular mechanism level (e.g., by enhancing binding), or to reduce degradation/lengthen half-life (e.g., by inhibiting a degradative enzyme) of the thing being activated Published work has established that RPPGF (SEQ ID NO:1) is highly stable in human plasma (11). RPPGF (SEQ ID NO:1) and its analogs can be used as vasoconstrictor agents in clinical circumstances of severe and acute, and/or chronic hypotension, such as occurs in endotoxemia secondary to bacterial sepsis. Additionally, congeners of the peptide or synthetic peptidomimetics and potentially, antagonists of the peptide target molecules (receptors, allosteric sites of enzyme activation or inhibition) are useful in the treatment of cardiovascular, metabolic or inflammatory diseases. It can be useful as a pharmacologic antagonist to bradykinin, acting as an analgesic and antiinflammatory agent in soft tissue or joints or around teeth, in sunburn and other burns, after topical application. These and other uses for RPPGF (SEQ ID NO:1), its analogs, agonists and antagonists are further described below.

A method of treating acute hypotension in a subject is provided. The method comprises administering to the subject a compound selected from the group consisting of RPPGF (SEQ ID NO:1), FGPPR (SEQ ID NO:2), analogs or mimetics thereof in an amount sufficient to sustain blood pressure. For example, the acute hypotension can be associated with endotoxemia secondary to bacterial sepsis. As shown in the present data, minikinin reduces hypotension and prolongs life in endotoxin stimulated shock.

A method of treating an inflammatory condition in a subject is provided, comprising administering to the subject an amount of a compound selected from the group consisting of RPPGF (SEQ ID NO:1), FGPPR (SEQ ID NO:2), analogs or mimetics thereof sufficient to reduce inflammation. For example, the inflammatory conditions treated include inflammatory arthritis, burns or the initiation of rhinorrhea, meningitis, pericarditis, pleuritis or vasculitis.

A method is provided for reducing pain in a subject, comprising administering to the subject a compound selected from the group consisting of RPPGF (SEQ ID NO:1), FGPPR (SEQ ID NO:2), analog or mimetics thereof in an amount sufficient to reduce pain (as the parent bradykinin is one of the most potent algesic substances known). The compound can be administered topically for the treatment of pain resulting from burns.

A method is provided for inhibiting osteoclastic activity in a subject, comprising administering to the subject a compound selected from the group consisting of RPPGF (SEQ ID NO:1), FGPPR (SEQ ID NO:2), analogs or mimetics thereof in an amount sufficient to reduce osteoclastic activity (as the parent bradykinin is one of the most potent osteoclastic substances known). For example, the osteoclastic activity can be the result of periodontal disease.

RPPGF (SEQ ID NO:1) or its analogs are antinatriuretic and antidiuretic agents in renal diseases. They can be used as an antiinflammatory and antisecretory agent in nasal sprays when kallikrein and kinins are participants in the initiation of rhinorrhea and other symptoms of the common cold. They can be used as an antidiarrheal agent after oral administration for the secretory diarrheas of intestinal infectious or inflammatory diseases, as kinins can cause secretory diarrheas.

Thus, a method of reducing electrolyte and water excretion in the kidney, gall bladder, and intestines of a subject is provided. The method comprises administering to the subject a compound selected from the group consisting of RPPGF (SEQ ID NO:1), FGPPR (SEQ ID NO:2), analogs or mimetics thereof in an amount sufficient to reduce electrolyte or water excretion. Thus, the electrolyte and water excretion associated with a secretory diarrhea can be reduced.

A method of inhibiting inducible nitric oxide synthase in a subject, comprising administering to the subject a compound selected from the group consisting of RPPGF (SEQ ID NO:1), FGPPR (SEQ ID NO:2), analogs or mimetics thereof in an amount sufficient to inhibit the activity of inducible nitric oxide synthase is provided.

A method of producing oscillations in the level of free intracellular calcium in a subject is provided, comprising administering to the subject a therapeutic amount of a compound selected from the group consisting of RPPGF (SEQ ID NO:1), FGPPR (SEQ ID NO:2) and analogs thereof. As described below, administration of RPPGF (SEQ ID NO:1) produces a rise in the level of free calcium that is followed by a lowering toward baseline. Thus, a method of increasing free intracellular calcium in a subject is provided, comprising administering to the subject an amount of a compound selected from the group consisting of RPPGF (SEQ ID NO:1), FGPPR (SEQ ID NO:2), analogs and mimetics thereof effective to increase intercellular free calcium.

A method of increasing DNA-synthesis in a subject is provided, comprising administering to the subject a DNA synthesis-increasing amount of a compound selected from the group consisting of RPPGF (SEQ ID NO:1), FGPPR (SEQ ID NO:2), analogs thereof.

A method of increasing tyrosyl phosphorylation of cytoplasmic proteins in a subject is provided, comprising administering to the subject a tyrosyl phosphorylation-increasing amount of a compound selected from the group consisting of RPPGF (SEQ ID NO:1), FGPPR (SEQ ID NO:2) and analogs thereof. In the method of increasing tyrosyl phosphorylase, the protein can be focal adhesion kinase.

A method of increasing prostaglandin synthesis in a subject is provided, comprising administering to the subject a prostaglandin synthesis-increasing amount of a compound selected from the group consisting of RPPGF, FGPPR and analogs thereof.

A method of increasing the generation of cyclooxygenase products in a subject is provided, comprising administering to the subject a cyclooxygenase product-generating amount of a compound selected from the group consisting of RPPGF (SEQ ID NO:1), FGPPR (SEQ ID NO:2) and analogs thereof.

A method of treating a condition which can be treated by an antikinin activity in a subject is provided, comprising administering to the subject an inhibitor of an enzyme which degrades the peptide consisting of RPPGF (SEQ ID NO:1). For example, the inhibitor can be an inhibitor of the enzyme prolyl endopeptidase. The conditions include but are not limited to, those described above.

A method of treating a condition associated with an antikinin activity of RPPGF (SEQ ID NO:1) in a subject is provided, comprising inhibiting an activity of RPPGF, whereby the condition associated with the activity of RPPGF (SEQ ID NO:1) is treated, and the condition is not associated with or caused by a thrombin inhibitor. Similarly, a method of treating a condition associated with an activity of RPPGF in a subject, comprising inhibiting the production of RPPGF (SEQ ID NO:1), whereby the condition associated with the activity of RPPGF (SEQ ID NO:1) is treated, and the inhibition is not via an ACE inhibitor. The activity can be an antikinin activity. This treatment can also be effected by administering a substance that stimulates production of or enhances the activity of enzymes, such as prolyl endopeptidase, which reduce the half-life of RPPGF.

Thus, the method comprises administering to the subject an activator of prolyl endopeptidase. The inhibition can be by an antagonist which binds RPPGF (SEQ ID NO:1). The inhibition can be by an antagonist which prevents the interaction of RPPGF with its receptor.

The list of conditions treated by inhibiting RPPGF includes diabetes, atherosclerosis, renal failure, stroke, cardiac failure and myocardial infarction. Others include, for example, those conditions that result from the effect RPPGF (SEQ ID NO:1) has on glial cells. As shown in the present data RPPGF (SEQ ID NO:1) dramatically affects the activity of glial cells of the rat brain. Glial cells are ubiquitous cells which surround and are in constant contact and communication with neurons. The present findings demonstrate that the pentapeptide, a product of an inflammatory reaction around neurons, for example, in Alzheimer's disease, Parkinson's disease or multiple sclerosis is likely to be affecting neuronal function. Inhibiting the activity of RPPGF (SEQ ID NO:1) can be therapeutic in such degenerative brain or nervous system diseases. Conversely, the pentapeptide or its analogs can be beneficial to neuronal function in some of these states.

A method of treating diabetes, atherosclerosis, renal failure, stroke, cardiac failure or myocardial infarction in a subject is provided, comprising inhibiting the production of RPPGF (SEQ ID NO:1) in the subject, whereby inhibiting the production of or shortening the half-life of RPPGF (SEQ ID NO:1) effects treatment of the above condition. This treatment can also be accomplished by administering an antagonist of RPPGF (SEQ ID NO:1).

A method of determining predisposition to a condition associated with an antikinin activity of RPPGF (SEQ ID NO:1) in a subject is provided, comprising measuring the amount of RPPGF (SEQ ID NO:1) in the plasma or serum of the subject and correlating the amount of RPPGF (SEQ ID NO:1) with predisposition to the condition. The condition can be hypertension, hypotension, renal failure, cardiac failure, natriuresis, diarrhesis, osteoclasis, autoimmune diseases or inflammatory diseases in a subject, comprising measuring the amount of a peptide consisting of RPPGF (SEQ ID NO:1) in the plasma or serum of the subject and correlating the amount of RPPGF (SEQ ID NO:1) with predisposition to hypertension, renal failure, cardiac failure, natriuresis, diarrhesis, osteoclasis or inflammatory diseases. The correlating step can involve comparing the RPPGF (SEQ ID NO:1) levels in patients known to have the disease with RPPGF (SEQ ID NO:1) levels in normal subjects. This information can be used to correlate the results for patients with the likelihood of developing hypertension. For example, a radioimmunoassay using radiolabeled (e.g., radioiodinated) RPPGF (SEQ ID NO:1), its analogs or anti-RPPGF antibodies as described herein can be used to measure RPPGF (see Example 5).

Antibodies to RPPGF (SEQ ID NO:1) can be made according to standard methods of antibody preparation (Harlow and Lane, latest edition). An example of an anti-RPPGF (SEQ ID NO:1) antibody is described in Shima et al. (11). The antibody can be labeled or used in conjunction with a labeled secondary antibody. Monovalent or single chain antibodies can be made, which bind RPPGF (SEQ ID NO:1).

There are many reasons for expecting this method of determining predisposition to hypertension to be useful. The first relates to the fact that the enzyme kallikrein, which is responsible for cleaving the parent bradykinin out of kininogen, is inversely correlated with blood pressure in hypertension and more importantly, in normal children studied longitudinally over many years. That is, normal children either black or white, have a level of kallikrein in their urine which is predictive of the rate at which their blood pressure will rise as they age. Thus, children with the lowest kallikreins have their BP track upwards as they age at a higher rate than children with the highest kallikreins. More recently, it has been shown that having high urinary kallikrein has a protective effect against hypertension and is one of the strongest major gene factors to be associated with essential hypertension (3,12–14).

Thus, measurement of the pentapeptide, and its own metabolite, RPP (SEQ ID NO:11), in biological fluids (e.g., urine, whole blood, plasma and cerebrospinal fluid) can be used to assess predisposition to hypertension or other disease, such as diabetes, atherosclerosis, renal failure, stroke, cardiac failure and myocardial infarction. For the same reasons, failure of the heart or kidneys—two organs well known to produce kinins and RPPGF, can also be subject to determination of predisposition by measuring RPPGF (SEQ ID NO:1) and/or RPP (SEQ ID NO:11) levels.

Administration

Parenteral administration, if used, is generally characterized by injection (intravenous, intradermal, subcutaneous and intramuscular). Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant level of dosage is maintained. See, e.g., U.S. Pat. No. 3,610,795, which is incorporated by reference herein.

Suitable carriers for parenteral administration of the substance in a sterile solution or suspension can include sterile saline that can contain additives, such as ethyl oleate or isopropyl myristate, and can be injected, for example, intravenously, as well as into subcutaneous or intramuscular tissues.

Topical administration can be by creams, gels, suppositories and the like. Ex vivo (extracorporeal) delivery can be as typically used in other contexts.

Oral administration is effective, particularly for synthetic non-peptide analogs of RPPGF (SEQ ID NO:1), e.g., for small molecule mimetics (1). Also, RPPGF (SEQ ID NO:1), FGPPR (SEQ ID NO:2) or peptide analogs having from one to five (d) amino acid substitutions, can be resistant to digestion, and can be administered orally.

Suitable carriers for oral administration include one or more substances which can also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers can be water, pyrogen free saline, pharmaceutically accepted oils, or a mixture of any of these. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel.

The substance can be administered to the subject in amounts sufficient to produce an antikinin activity or to inhibit or reduce an antikinin activity. Optimal dosages used will vary according to the individual, on the basis of age, size, weight, condition, etc, as well as the particular modulating effect being induced. One skilled in the art will realize that dosages are best optimized by the practicing physician and methods for determining dosage are described, for example, in *Remington's Pharmaceutical Sciences* [Martin, E. W. (ed.) *Remington's Pharmaceutical Sciences*, latest edition Mack Publishing Co., Easton, Pa.]. Treatment can be continued for an indefinite period of time, as indicated by monitoring of the signs, symptoms and clinical parameters associated with a particular activity of the antikinin or inhibitor of the antikinin.

For example, the amount of the peptide or analog can be from about $10^{-9}$ to $10^{-6}$ molar. The amounts showing activity range from $10^{-9}$ to $10^{-6}$ molar, depending upon assay systems being used, that is, vascular smooth muscle cells, brain glial cells, etc.

The following examples are intended to illustrate, but not limit, the invention. While the protocols described are typical of those that might be used, other procedures known to those skilled in the art may be alternatively employed.

EXAMPLES

Example 1

Activity of RPPGF
Mean Systemic Arterial Blood Pressure

Experiments were performed on male spontaneously hypertensive rats weighing 250–350 g. Anesthesia and surgical procedures are described (15–17). Following the surgical procedures, animals were allowed to stabilize for 30 minutes. Injections were then made unilaterally into the rostral ventral lateral medulla oblongata. In any given experiment, not more than four doses of the BK fragments were given. Successive injections were alternated between sides after an intervening period of 20 minutes. Mean arterial pressure was measured from a femoral arterial line with a transducer (Statham Laboratories, Inc. Hato Rey, Puerto Rico) and recorded using a polygraph (Grass Instrument Co., Quincy, Mass.). Values shown are the mean changes ± sem.

Figure 1:
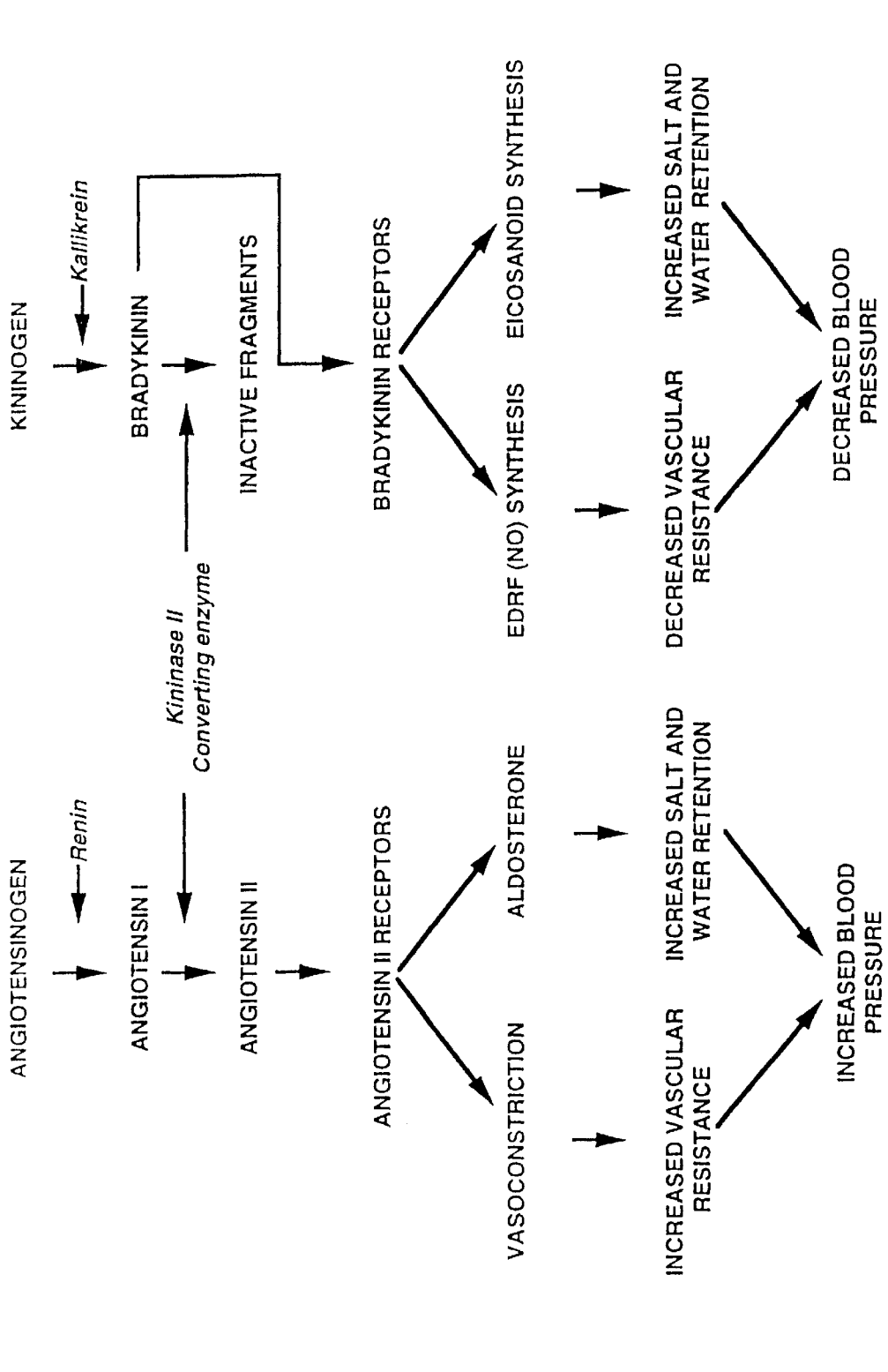
FIG. 1 shows the angiotensinogen/renin/angiotensin and kininogen/kallikrein/kinin systems in control of blood pressure.
Figure 2:
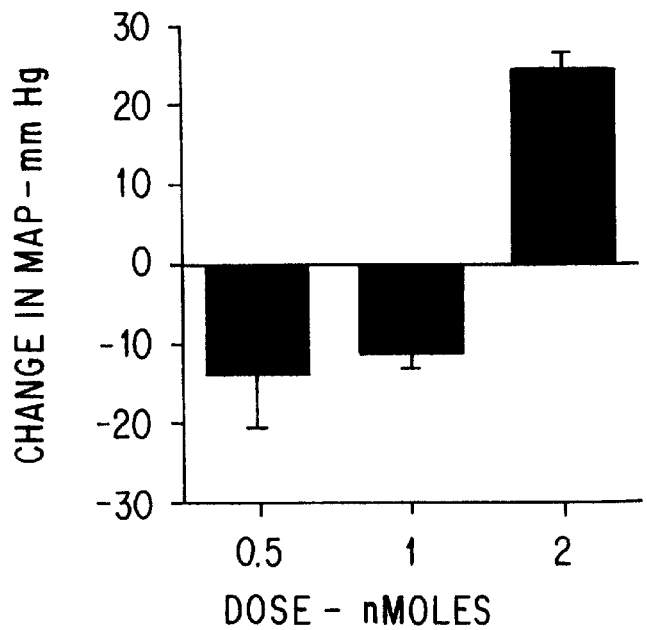
FIG. 2 shows the mean systemic arterial blood pressure responses to RPPGF (SEQ ID NO:1) (bradykinin fragment 1-5) in hypertensive anesthetized rats.

FIG. 2 shows that this fragment of bradykinin is able to lower systemic mean arterial pressure (MAP) in low doses, but increase it in a higher dose after brain intracerebroventricular injections in anesthetized rats.

Figure 3:
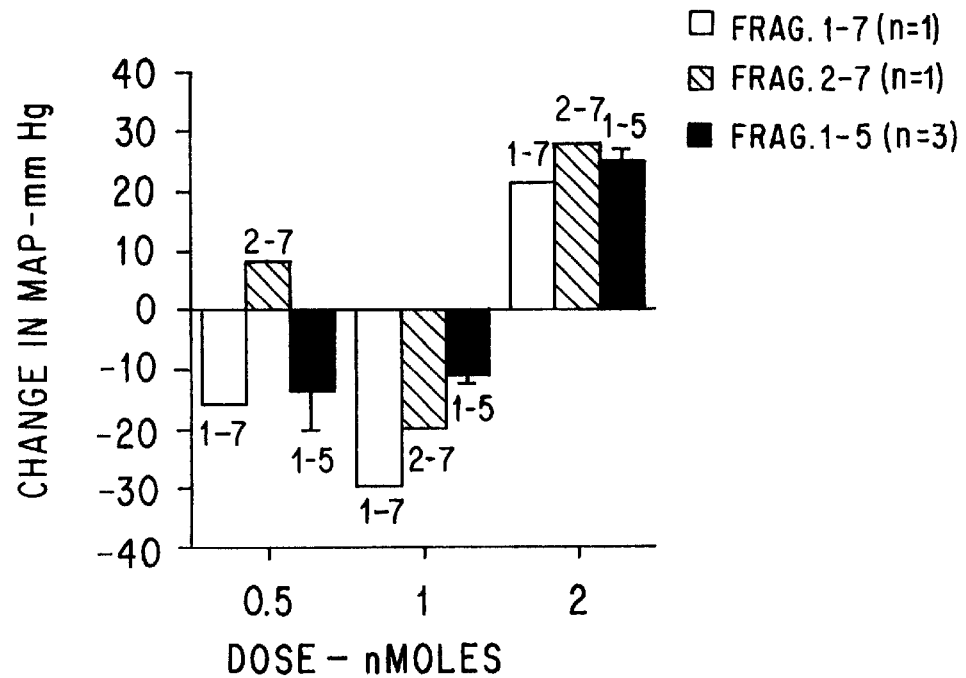
FIG. 3 shows the mean systemic arterial blood pressure responses to RPPGF (SEQ ID NO:1) compared to RPPGFSP (SEQ ID NO:3) and PPGFSP (SEQ ID NO:4) in hypertensive anesthetized rats.

FIG. 3 shows that other, heretofore considered inactive bradykinin fragments, for example $BK_{1-7}$ and $BK_{2-7}$ also affect systemic blood pressure in these preliminary experiments.

Effect of RPPGF on Levels of Free Intracellular Calcium

Figure 4:
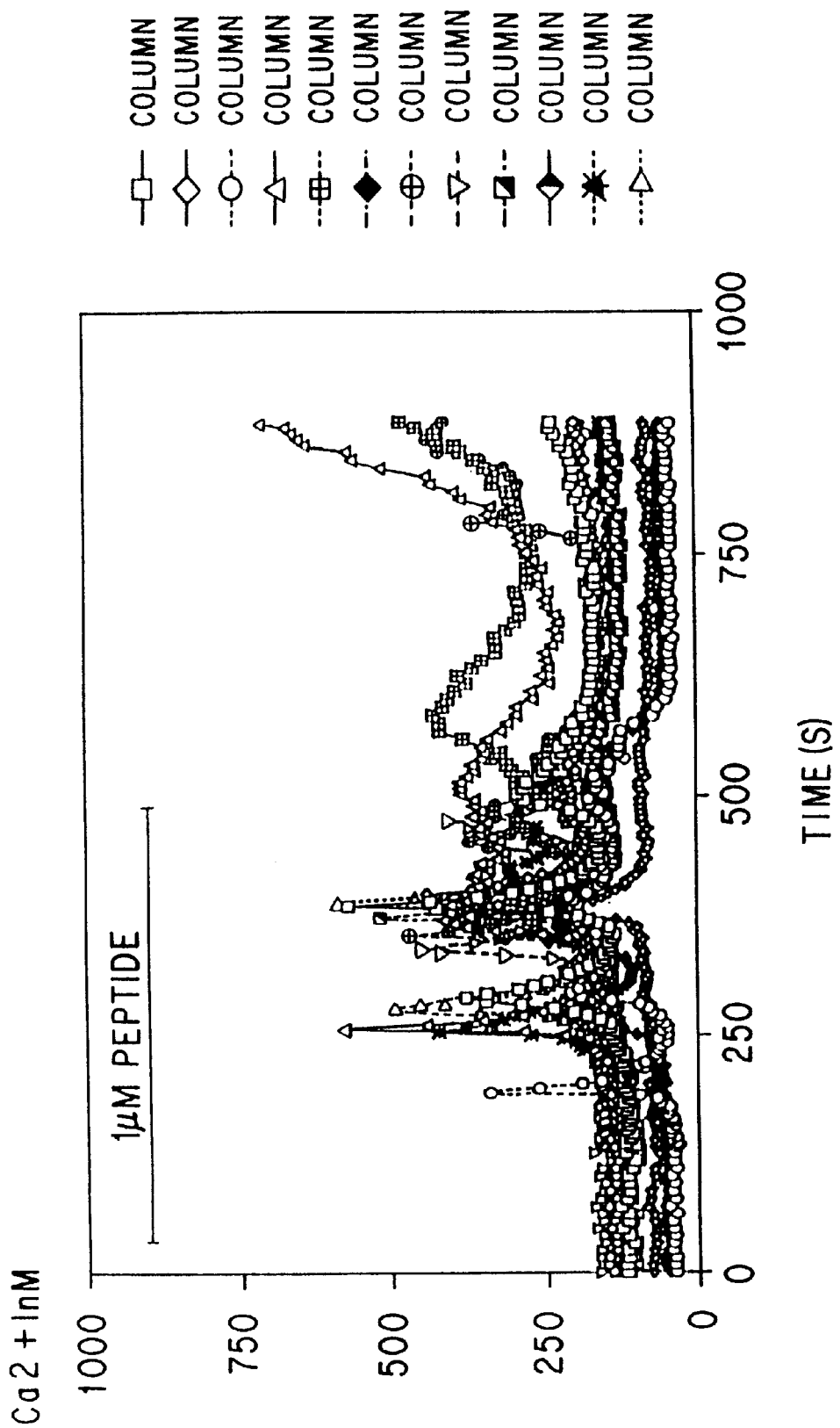
FIG. 4 shows the effect of RPPGF (SEQ ID NO:1) upon levels of free intracellular calcium in rat brain cortical glial cells. Time in seconds is on the horizontal axis. Each symbol represents an individual glial cell in culture being exposed to RPPGF $10^{-6}$ M, in surrounding nutrient medium from 72 seconds after beginning to measure calcium level, to 505 seconds, when the perfusate is switched back to control medium.
Figure 5B:
FIG. 5 shows the effect of RPPGF (SEQ ID NO:1) upon levels of free intracellular calcium a typical cell (#1), of the field of cells being observed in the lower right hand corner. Time in seconds is on the horizontal axis. The concentration of RPPGF being perfused from 120 seconds to 720 seconds is $10^{-8}$M. Note the cyclic changes, "oscillations", in calcium titrations, a known, but now well understood phenomenon.
Figure 5A:
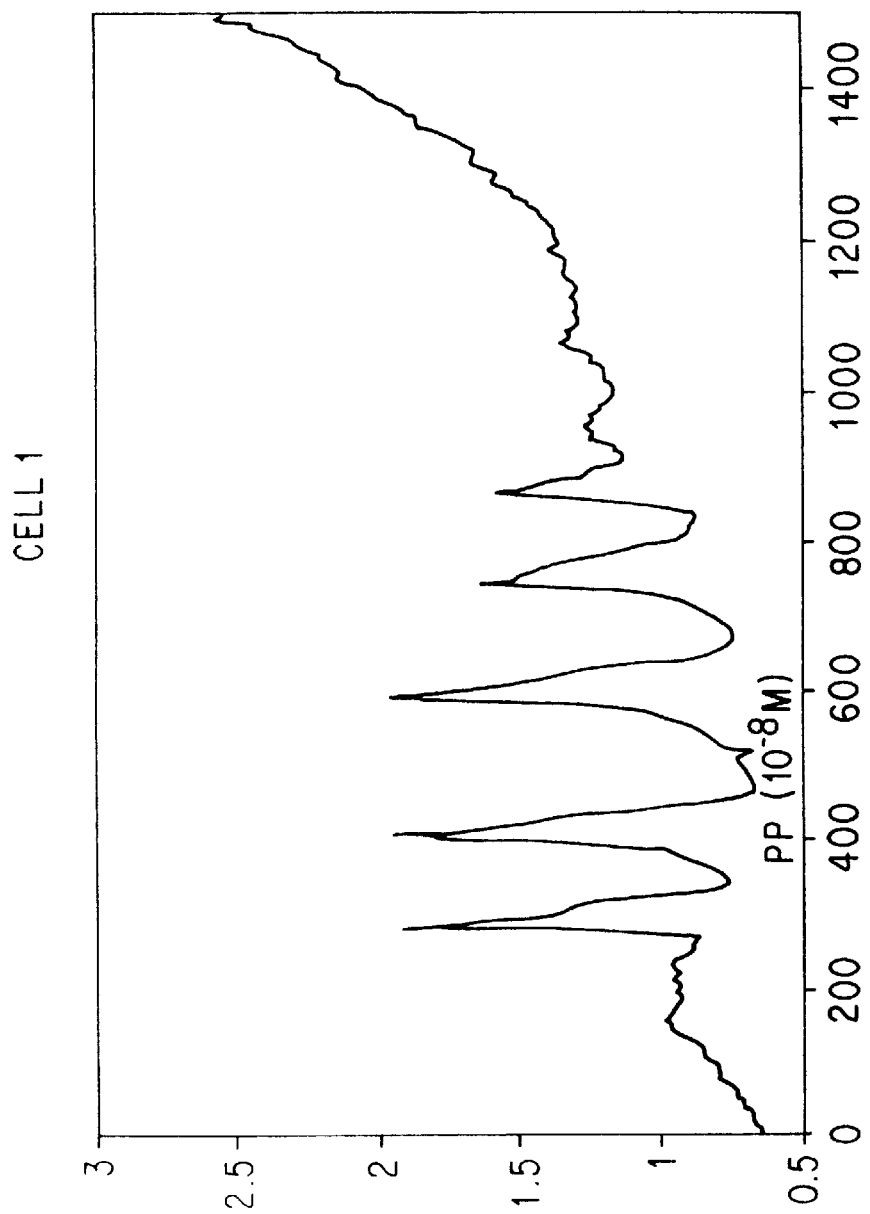

FIGS. 4 and 5 show that when RPPGF (SEQ ID NO:1) is perfused over cultured rat brain cortex glial cells, which in situ surround, communicate with and protect brain nerve cells and their processes, there is a striking and abrupt change in the level of free intracellular calcium within these cells. The changes are measured in real time via alteration in the fluorescence of a calcium sensitive dye which accumulates in the cells during a preincubation period. These dramatic responses are unlike any responses generated by the parent bradykinin. They signify a potentially extremely important interplay between bradykinin liberation at sites of inflammation, either extrinsic to, or within the nervous system, and the possibility that fragments of the locally catabolized kinin act upon these supporting elements of the nervous system. These effects can signify a protective homeostatic response by which glial cells act to sustain neuronal integrity in circumstances of local acute or chronic inflammation and insult, such as occurs in meningitis or Alzheimer's disease.

Cell Culture

Rat aortic VSMC from male Sprague-Dawley rats (Charles-River, Laboratories, Wilmington, Mass.) were prepared by a modification of the method of Majeck et al. (2). A 2 cm segment of artery cleaned of fat and adventitia was incubated in 1 mg/ml collagenase for 3 hours at room temperature. The artery was then cut into small sections and fixed to a culture flask for explantation in minimal essential media (MEM) containing 10% fetal calf serum (FCS), 1% non-essential amino acids, 100 mU/ml penicillin and 100 µg/ml streptomycin. Cells were incubated at 37° C. in a humidified atmosphere of 95% air-5% $CO_2$. Medium was changed every 3–4 days and cells were passaged every 6–8 days by harvesting with trypsin-EDTA. Cell viability was assessed by standard dye exclusion techniques using 1% trypan blue. VSMC were identified by the following criteria. They stained positive for intracellular cytoskeletal fibrils of actin and smooth muscle cell specific myosin (indicative of contractile cell) and negative for factor VIII antigens. VSMC isolated by this procedure were homogeneous and were used in all studies between passage 2–4.

DNA Synthesis (Thymidine Incorporation)

DNA synthesis was assessed by measuring incorporation of $^3$H-thymidine into DNA fragments. Quiescent VSMC grown in 24-well plates in serum free media were stimulated with mini-kinin ($10^{-9}$–$10^{-6}$ M) for 18-h, and then pulsed for 4-h with 1 µCi/ml/well of $^3$H-thymidine. The experiment was terminated by addition of 0.5 ml of 0.3 M perchloric acid for 30 seconds followed by a cold saline wash. Cells were solubilized in 0.1-1-SDS/0.1N NaOH, and incorporated radioactivity was quantified.

Binding Assays

VSMC grown in 6-well plates were washed with and allowed to equilibrate with 1 ml of binding buffer (25 mM TES, 1 mM phenanthroline, 15 μM captopril, 0.1% BSA, pH 7.0). Saturation binding experiments were performed by incubating cells with [$^{-3}$H] bradykinin (60,000 cpm/well) and varying the concentration of unlabeled bradykinin ($5 \times 10^{-11} - 1 \times 10^{-6}$ M) in binding buffer for 2 h at 4° C. Cells were washed 3 times with 2 ml of ice-cold binding buffer and solubilized for 10 min in 1% SDS, 0.1 M NaOH, 0.1 M $Na_2CO_3$ solution and counted for radioactivity. Data were analyzed using the LIGAND program to determine the affinity constants and the receptor number.

Immunoprecipitation and Immunoblotting

VSMC grown in 10 cm dishes and stimulated with pentapeptide (0.1 μm) were suspended in 250 μl of lysis buffer (20 mM Tris, 130 mM NaCl, 10% glycerol, 10 mM Chaps, 1 mM PMSF, 2 mM Na vanadate, 100 mU/ml aprotinin, 0.15 mg/ml benzamidin, pH 8.0), sonicated for 10 sec and centrifuged at 13,000 g for 10 min. The supernatant was harvested as the cytosolic fraction. A quantity of 25–30 μg of the cytosolic fraction was analyzed by SDS-polyacrylamide gel electrophoresis and the separated proteins were transferred to polyvinylidine difluoride (PVDF) membranes. The membranes were immunoblotted with a recombinant anti-phosphotyrosine (anti-PY RC 20H) antibodies (1:5000 dilution, Transduction Laboratories). Immunoreactive bands were visualized using the enhanced chemiluminescence reagent (ECL, Amersham) according to the procedure described by the supplier. The protein concentration in the cytosolic fractions was determined by assay of Lowry et al.

To examine the effects of pentapeptide on the tyrosine phosphorylation of focal adhesion kinase (p125FAK), 250 μg of soluble protein obtained as described above was preincubated for 5 min with 10 μl of 10% pansorbin. The suspension was centrifuged for 4 min at 10,000 rpm and to the resulting supernatant, 500 μl of immunoprecipitation buffer (1.5% triton X100, 150 mM NaCl, 10 mM Tris, 1 mM EDTA, 1 mM EGTA, 0.5% NP-40, 0.2 mM Na vanadate, 0.2 mM PMSF, pH 7.4) and 5 μg of anti-p125FAK antibodies were added and incubated overnight at 4° C. The immunocomplex was recovered by incubating with 50 μg Pansorbin at room temperature for 30 min, followed by centrifugation at 10,000 rpm for 4 min. The pellet containing the immunocomplex was resuspended in 20 μl of SDS sample buffer, boiled for 5 min, spun and analyzed by SDS-PAGE. The separated immunocomplex was transferred to PVDF membranes and immunoblotted with anti-phosphotyrosine antibodies (1:5000 dilution). The tyrosine phosphorylated p125FAK band was visualized using ECL reagent as described above and the intensity of the band was quantified by a microdensitometer.

Figure 6:
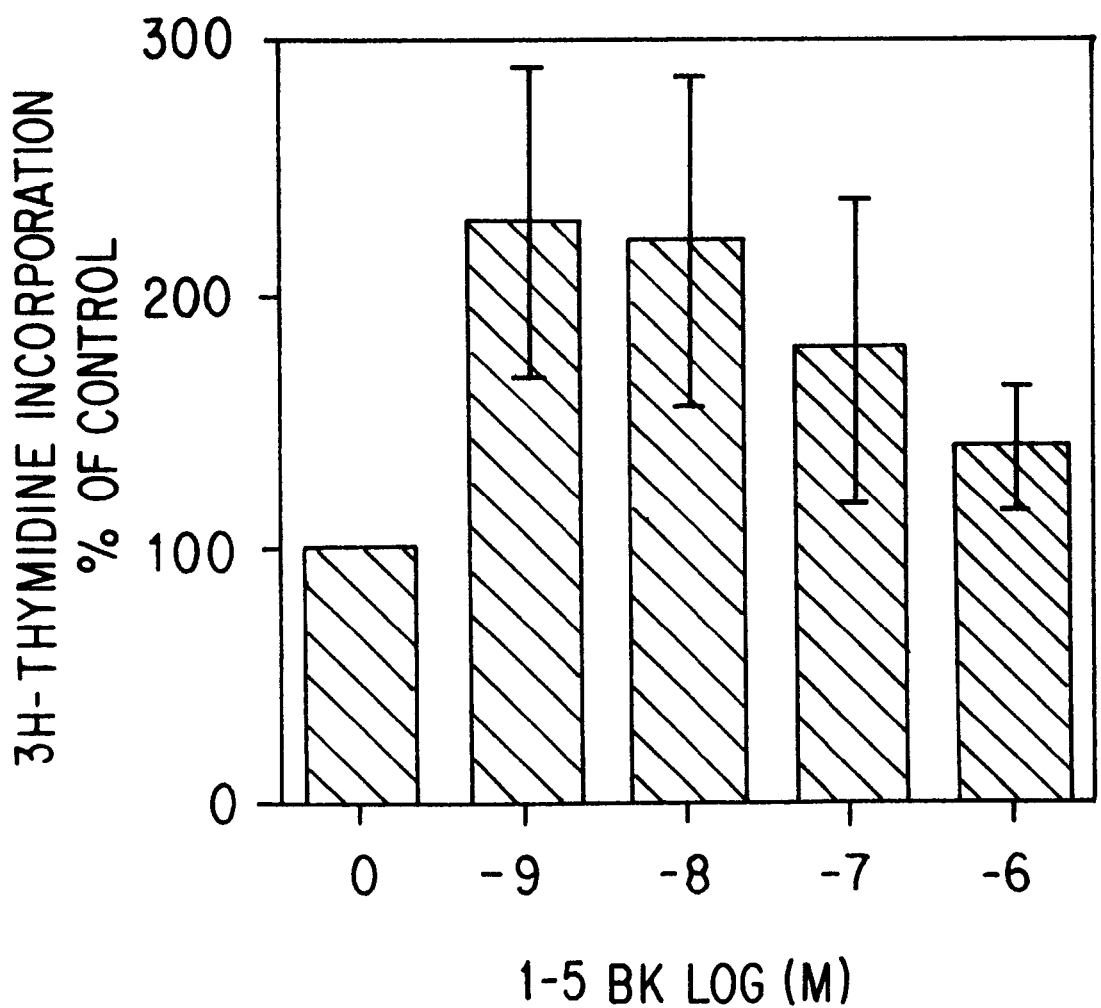
FIG. 6 shows the effect of RPPGF (SEQ ID NO:1) on DNA synthesis in rat aortic smooth muscle cells. The data are means from six experiments. RPPGF (SEQ ID NO:1) in concentrations from $10^{-9}$M to $10^{-6}$M produces marked increases in new DNA synthesis with the greatest stimulation noted at the lowest concentration tested.

FIGS. 6 and 7, and tyrosine phosphorylation experiments show that RPPGF (SEQ ID NO:1) has striking effects upon arterial smooth muscle cells in culture. First, there is a dramatic increase in DNA synthesis in response to very low concentrations ($10^{-9}$M) of RPPGF (FIG. 6). Secondly, the peptide produces this effect without action upon the receptors for the parent peptide, bradykinin (FIG. 7,a,b,c). Thirdly, the peptide induces, within a 5-minute exposure to these vascular smooth muscle cells, a pronounced increase in tyrosyl phosphorylation of numerous cytoplasmic and nuclear proteins. Unstimulated control cells showed no significant labeled bands. The response to RPPGF ($10^{-7}$M) is striking and differs from that of bradykinin and des-Arg$^9$-BK. Fetal calf serum (FCS) was used as a positive control. In particular, RPPGF (SEQ ID NO:1) produces tyrosyl phosphorylation of a specific protein called "focal adhesion kinase", an integral participant in intercellular matrix formation. RPPGF, $10^{-7}$M, produces activation of this specific kinase which is more intense than that of BK or des-Arg-$^9$-BK. FCS was used as a positive control. This process is obligatory to cell growth and tissue integrity, notably in circumstances of vascular remodeling such as after myocardial infarction, in hypertension, or in diabetic renal and vascular disease.

Nitric Oxide Measurement-Greiss Reaction for $NO_2$-

VSMC preincubated with RPPGF for 15 min, were treated with LPS (50 μg) or IL-1β (1 ng/ml) for 24 hr. Nitric oxide activity was measured in the media by the Greiss reaction. Briefly, mix 0.9 vol. sample (or standard) with 0.1 vol. Greiss reagent (e.g. 1 ml sample+0.1 ml 10× Greiss reagent). Let stand for 10 min at room temperature, read absorbance at 550 nm, and determine concentration by comparing to known standards. The reagent components are set out below.

Figure 9A:
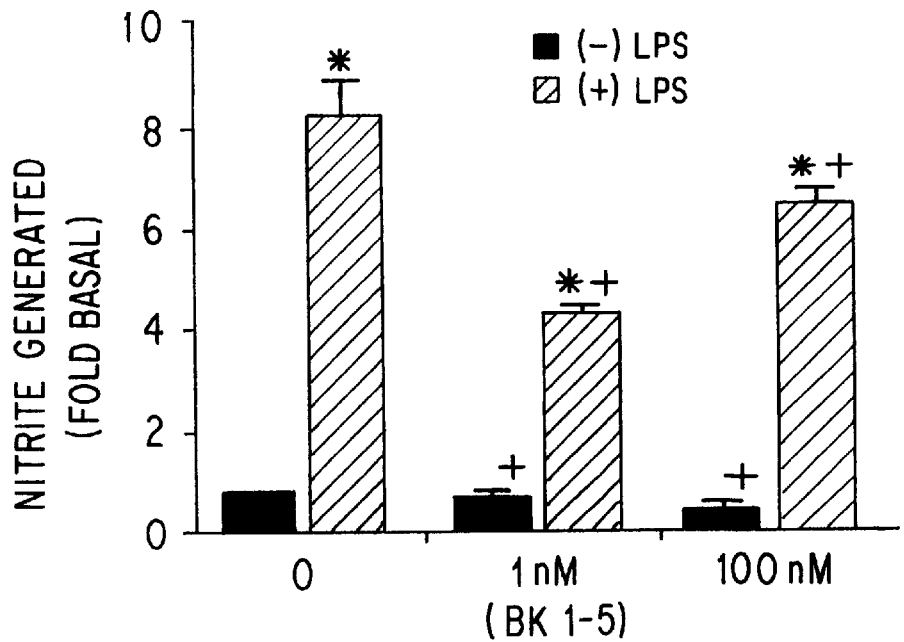
FIG. 9A shows RPPGF (SEQ ID NO:1) (BK1-5) inhibits generation of nitric oxide in cultured rat aorta smooth muscle cells. LPS (lipopolysaccharide) initiation of the septic response is generated via several mediators. One of these, thought to be responsible for LPS-induced deterioration of vascular integrity, is nitric oxide. The nitric oxide generated is a consequence of increased expression of the inducible form of nitric oxide synthase (iNOS). The induction of this isoform of nitric oxide synthase is the result of cellular exposure to cytokines, such as interleukin 1β (IL-1β), and to LPS. Primary cultures of vascular smooth muscle cells were exposed to LPS (50 µg/ml) in the absence, or presence of BK1-5. After 24 hours of exposure quantitation of nitrite in the media by the Greiss reaction was used as a measure of nitric oxide generation. This data shows that BK1-5 inhibits the generation of NO from cultured smooth muscle cells.
Figure 9B:
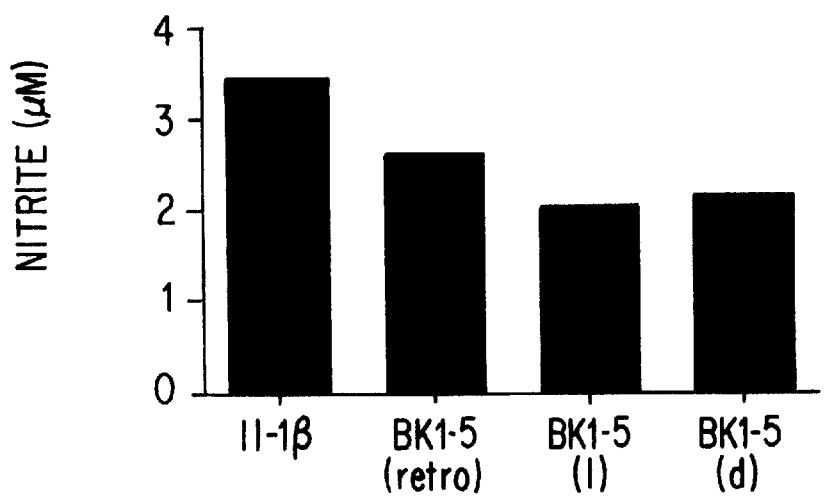
FIG. 9B shows RPPGF (SEQ ID NO:1) (BK1-5) inhibits generation of nitric oxide in cultured rat aorta smooth muscle cells under the experimental conditions described for FIG. 9A. Primary cultures of vascular smooth muscle cells were exposed to IL-1β (10 µg/ml) in the absence or presence of either (l)-, (d)-, or (retro)-BK1-5. This data shows that BK1-5 inhibits the generation of NO from cultured smooth muscle cells.

Greiss Reagent (10×):
   1.0 g sulfanilamide (p-aminobenzenesulfonamide)
   0.1 g naphthylethylenediamine
   2.5 ml phosphoric acid
   Bring volume to 10 ml with dd $H_2O$ Standards:
   1–100 μM $NaNO_2$
   Make up in sample medium as serial dilutions $No_2$ Sample Medium:
   1% Triton×400
   150 mM NaCl
   10 mM Tris
   1 mM EDTA
   1 mM EGTA
   0.5% NP-40
   0.2 mM Na Vanadate
   0.2 mM PMSF The pentapeptide inhibits inducible nitric oxide synthase in vascular smooth muscle (FIG. 9). Inducible nitric oxide synthase was induced by LPS (lipopolysaccharide), the principal component of bacterial endotoxin, in the presence or absence of the pentapeptide, and the effect of the pentapeptide on nitrite levels was measured. A reverse dose response curve was observed. At $10^{-7}$M RPPGF (SEQ ID NO:1), significant inhibition occurred, while at $10^{-9}$M even more inhibition was found. Additionally, both the all (d) amino acid pentapeptide and the "retro" pentapeptide (FGPPR (SEQ ID No:2)) inhibited nitric oxide production in a response to a second activator of inducible nitric oxide synthase, IL-1β (FIG. 8b). In light of these results, RPPGF can block nitric oxide formation in blood vessels.

Activation of Cyclooxygenase

Monolayers of cultured vascular smooth muscle cells grown in 12-well plates, were maintained in Dulbecco's minimal essential media (DMEM) containing 10% fetal bovine serum (FBS) until confluent. Cells were then exposed overnight to DMEM containing 0.1% FBS. The monolayer was washed and exposed to the agents of interest in serum free DMEM for 10 minutes at 37° C. The media was removed, frozen and saved for assay. 6-ketoPGF$_{1\alpha}$ released into the media was measured by radioimmunoassay using previously published techniques (18). The amount of 6-ketoPGF$_{1\alpha}$ released was corrected for total cell protein in each sample.

Figure 10A:
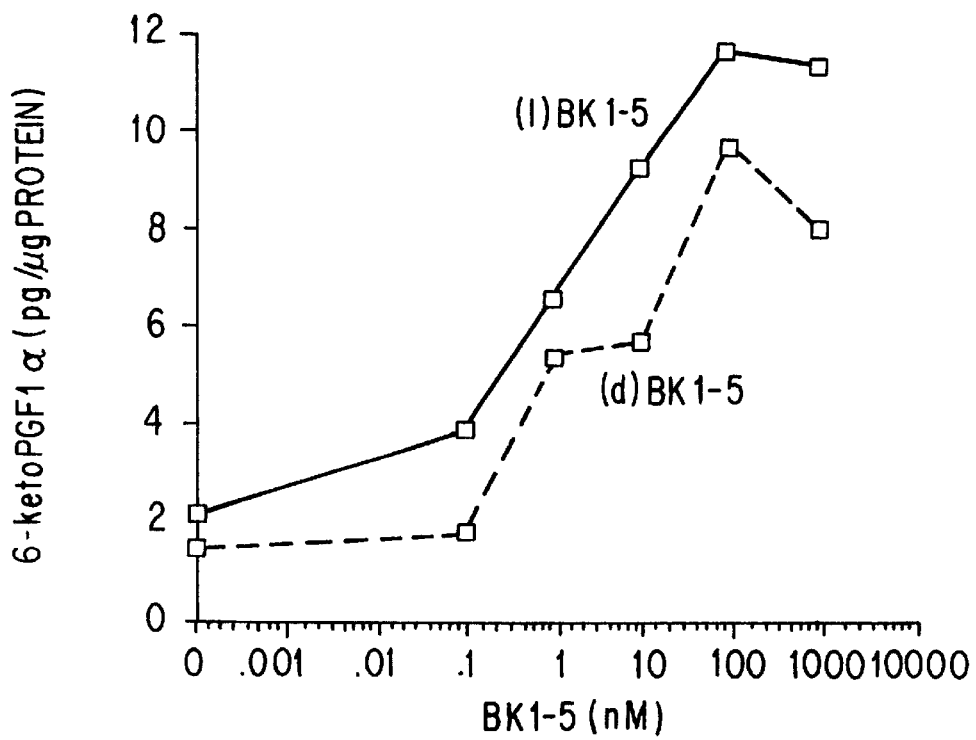
FIG. 10A shows activation of cyclooxygenase by both (l)- and (d)-RPPGF (SEQ ID NO:1) (BK1-5) in cultured rat aortic vascular smooth muscle cells. Confluent monolayers of cells were stimulated by the indicated concentrations of agents. Generation of 6-keto-PGF$_{1\alpha}$ was measured in the media by radioimmunoassay as a measure of cyclooxygenase activity. Concentration response curve to (l)- and (d)-BK1-5, n=2. Values shown are fold increases in 6-keto-PGF$_{1\alpha}$ produced by the agents compared to that seen under basal conditions. These data shown that both (l)- and (d)-BK1-5 activate cyclooxygenase and enhance the ability of AII and BK to stimulate cyclooxygenase.
Figure 10B:
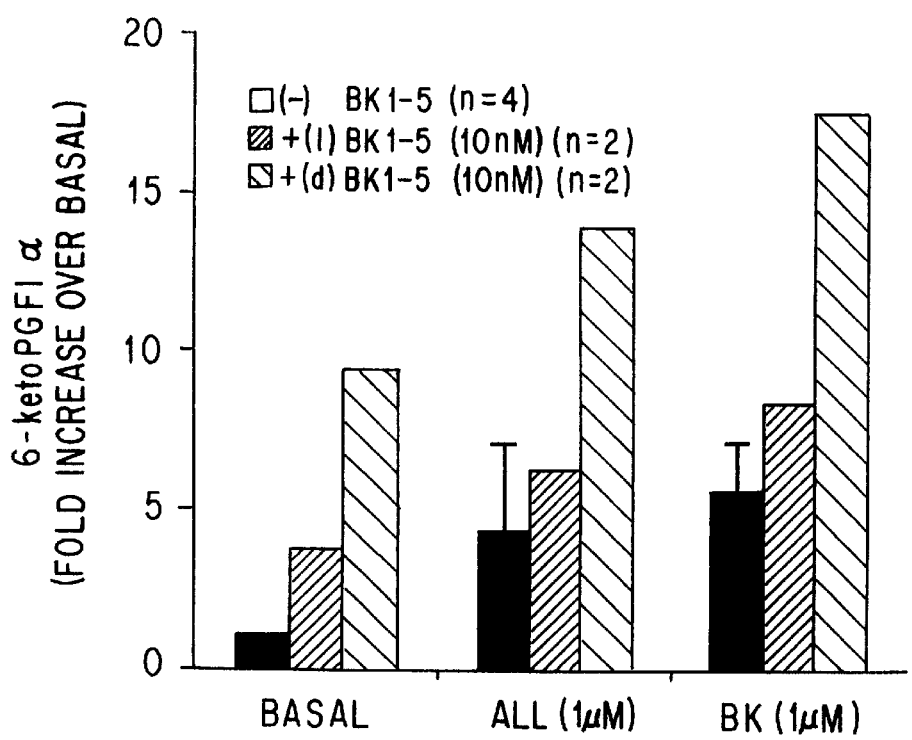
FIG. 10B shows activation of cyclooxygenase by both (l)- and (d)-RPPGF (SEQ ID NO:1) (BK1-5) in cultured rat aortic vascular smooth muscle cells. Confluent monolayers of cells were stimulated by the indicated concentrations of agents. Generation of 6-keto-PGF$_{1\alpha}$ was measured in the media by radioimmunoassay as a measure of cyclooxygenase activity. Effect of 10 nM (l)- or (d)-BK1-5 on activation of cyclooxygenase by angiotensin II (AII) and bradykinin (BK). Values shown are fold increases in 6-keto-PGF$_{1\alpha}$ produced by the agents compared to that seen under basal conditions. These data shown that both (l)- and (d)-BK1-5 activate cyclooxygenase and enhance the ability of AII and BK to stimulate cyclooxygenase.

FIG. 10 shows that both the (1) and the (d)-pentapeptide activate the enzyme cyclooxygenase in cultured rat aortic smooth muscle cells. The pentapeptide analogs ((d) and (1)-BK1-5) produced a concentration-dependent increase in the amount of 6-keto PGF$_{1\alpha}$ released from the cultured cells. Additionally, both (d) and (l)-BK1-5 enhanced the generation of 6-keto PGF$_{1\alpha}$ produced by two recognized activators of prostaglandin synthesis, angiotensin II and the pentapeptide parent hormone, bradykinin.

Both (l)- and (d)-RPPGF (BK1-5) (SEQ ID NO:1) protect against LPS

Measurements of aortic contractions in response to phenylephrine were performed as previously described (19). Briefly, aortae were removed from anesthetized male Sprague-Dawley rats, cleaned of adventia, cut into 5 mm segments and hung under 1.5 grams of tension in a 10 ml organ bath. The segments were equilibrated for one hour in Kreb's Henseleit solution followed by stimulation by potassium chloride (50 mM), wash out and a return to baseline conditions. Forty-five minutes later, an initial concentration-response curve to phenylephrine was performed on each segment. Integrity of the endothelium was tested by the presence of relaxation in response to acetylcholine (10 µM) subsequent to contraction by phenylephrine. The agents were washed out of the organ bath and segments were allowed to re-equilibrate for 1 hour. BK1-5 or saline was added fifteen minutes prior to the addition of LPS or in control segments, saline. The segments were incubated for 5 hours with 2 changes of buffer and re-addition of agents. A concentration-response curve was then performed with phenylephrine. Data presented is the mean ± sem from the indicated number of segments stimulated with phenylephrine at the end of the 5 hour incubations. Comparisons were made using ANOVA for repeated measures (panel A) and ANOVA with Fisher's post hoc t-test (panel B). Tension produced was corrected for the dry weight of each segment.

Figure 11A:
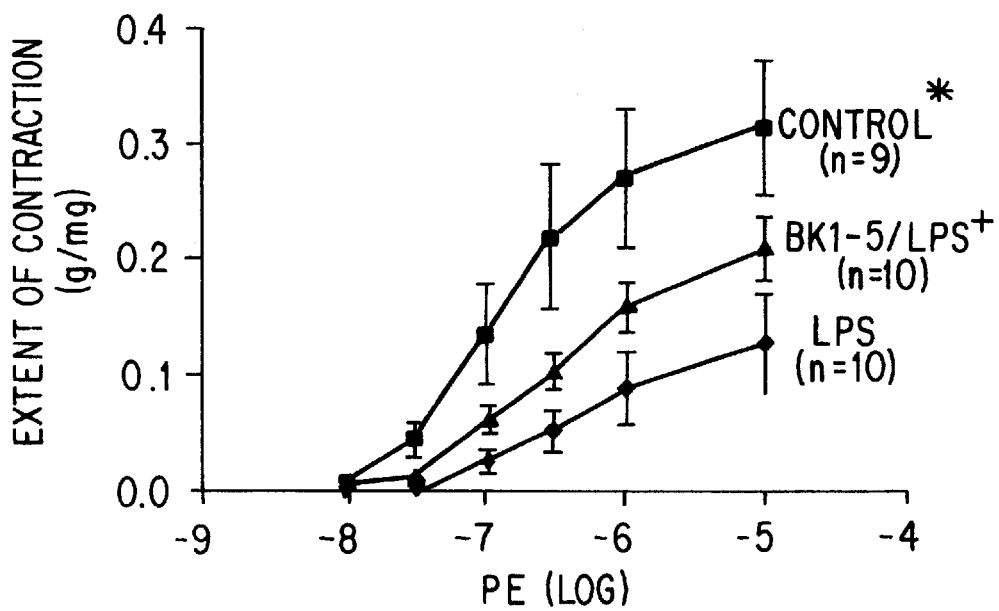
FIG. 11A shows that both (l)- and (d)-RPPGF (SEQ ID NO:1) (GK1-5) protect against the deleterious effects of endotoxin (LPS) on isolated rate aorta. (l)-BK1-5 and (d)-BK1-5 were examined for their ability to protect aortic segments from the adverse effects of endotoxin (lipopolysaccharide, LPS) exposure. LPS treatment of aortic segments results in decreased responsiveness to various contractile agents. Aortae were isolated from male Sprague-Dawley rats, cut into 5 mm segments, hung in Kred's-Henseleit solution in organ chambers under 1.5 gms tension. Segments were exposed to LPS (30 µg/ml), either (l)- or (d)-BK1-5 (1 nM) plus LPS, or vehicle alone (control) for 5 hours. At the end of the incubations, contractile integrity of the segments was measured in response to increasing concentrations of phenylephrine. In panel A, treatment with LPS resulted in significant deterioration of the contractile responses to phenylephrine. However, treatment of segments with (l)-BK1-5 along with LPS protected contractility. Segments treated with BK1-5 alone responded similarly to control segments. Thus, in these studies, both (1)- and (d)-BK1-5 protected isolated aortic segments against the deleterious effects of LPS.
Figure 11B:
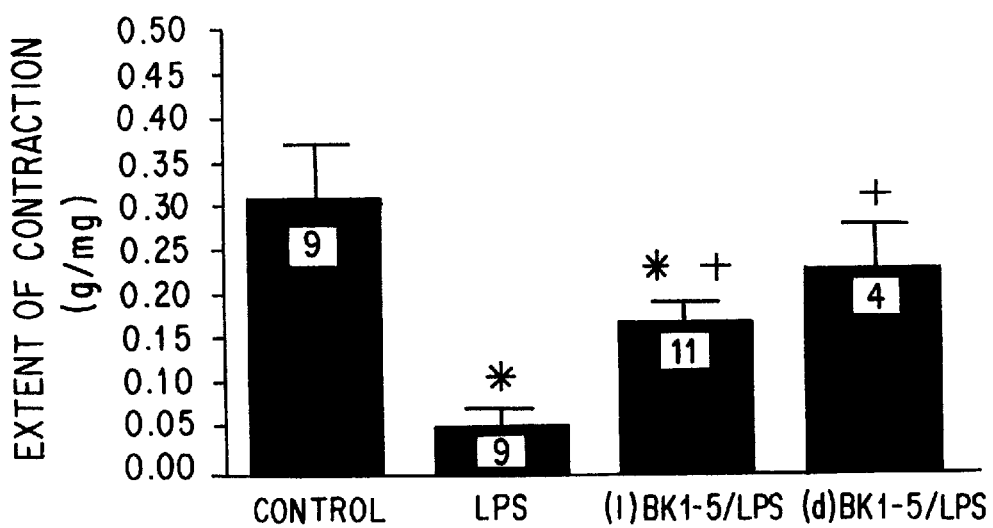
FIG. 11B shows protection against the deleterious effects of LPS by both (l)- and (d)-BK1-5 upon stimulation by 1 µl phenylephrine in the experiments described above.

In experiments in isolated rat blood vessels, both the (d) and the (l) pentapeptide sustained vascular integrity in the face of attack by LPS (FIG. 11).

Effect of RPPGF and its Analogs in Response to LPS

Male Sprague-Dawley rats (220–480 g) were anesthetized with inactin (120 mg/kg, IP). The trachea was cannulated and the animal was allowed to breath 100% O$_2$. Polyvinyl cannulas (Norton Plastics, Akron, Ohio) were inserted into the jugular vein and the femoral artery for the purposes of infusion of saline and agents and for monitoring of blood pressure, respectively, as described for FIGS. 2 and 3. Heart rate was monitored by tachograph and body temperature was maintained at 37° C. After a 2 hour period of equilibration with saline infusion (0.25 ml/hr), peptides (1 µg/kg followed by 143 ng/kg/hr) or saline were administered, followed one hour later by LPS (12 mg/kg). Time of death was taken as time after administration of LPS when there was no longer a detectable ECG. Values shown are the mean ± sem from the indicated number of studies and were compared using either t-test (FIG. 12A) or ANOVA with Fisher's post-hoc t-test (FIG. 12B). FIG. 13 shows results for time-dependent changes in mean blood pressure in rats treated with LPS.

In anesthetized rats, administration of (l), (d)-, or the retropentapeptide prolonged cardiovascular integrity and life in an animal treated with endotoxin, compared to an animal treated with endotoxin alone, whereas, treatment with the parent hormone bradykinin or a scrambled pentapeptide (altered amino acid sequence) did not prolong life in this model (FIG. 12). FIG. 13 shows the effect of the pentapeptide on basal median arterial blood pressure in LPS induced shock. FIG. 13 shows the effect of the pentapeptide on heart rate in LPS induced shock.

Synthesis of Radioiodinated RPPGF (BK1-5) (SEQ ID NO:1)

Synthesis of N$^\alpha$($^{125}$I-des-NH$_2$-Tyr)BK1-5 was carried out according to previously published protocols (20) using commercially available Bolton-Hunter reagent (Pierce, Rockford, Ill.) and standard chloramine-T iodination with Na$^{125}$I (2200 Ci/mMole, NEN). Methods for purification of products by HPLC and for their characterization were as described in FIG. 14 legend.

Example 2

Screening for Mimetics of RPPGF

Intracellular Calcium Measurements

RPPGF (SEQ ID NO:1) was shown to stimulate increases in intracellular free calcium in cultured rat brain cortical cells. This assay can be used to screen for analogs and mimetics of RPPGF (SEQ ID NO:1). The measurement of intracellular free calcium is performed using the fluorescent calcium probe Fura-2 according to previously published methods (21). In addition to using cultured rat brain cortical cells, additional cultured cells can be employed such as, rodent vascular smooth muscle cells, human umbilical vein endothelial cells, bovine pulmonary endothelial cells, rodent fibroblasts, and clonal cell lines such as the neonatal rat aortic vascular smooth muscle cell line A7r5 and others.

Platelet Aggregation Studies

RPPGF (SEQ ID NO:1) and [analogue mimetics] are tested for their ability to either stimulate platelet aggregation or inhibit platelet aggregation produced by other platelet agonists such as ADP, collagen or thromboxane A2. The method for performing these screening assays would employ previously published procedures (22). The source of the platelets can be human, rodent, rabbit or porcine or others.

Cyclic-AMP Assays

RPPGF (SEQ ID NO:1) and [analogue mimetics] are tested for their ability to either stimulate adenylyl cyclase or inhibit adenylyl cyclase stimulation produced by other agonists such as isoproterenol or prostacyclin mimetics according to previously published methods (23). The sources of cells used as targets for this screening can be one or more of the following cultured cells derived from vascular smooth muscle, endothelium, fibroblasts or mesanglum: or tissues such as; segments of aorta or isolated platelets. The sources for the cells and/or tissues can include, but are not limited to, human, rodent, rabbit, porcine or others.

Rodent Aortic Ring Contraction

RPPGF (SEQ ID NO:1) and analogue mimetics are tested for their ability to either stimulate rodent aortic ring contraction or provide protection of aortic rings against the effects of endotoxin or other pathological agents according to previously published methods (19, 24).

Cyclooxygenase Assays

RPPGF (SEQ ID NO:1) and analog mimetics are tested for their ability to either stimulate cyclooxygenase-1 or cyclooxygenase-2 or inhibit stimulation of cyclooxygenase-1 or cyclooxygenase-2 by known agonists by previously published methods (18). The source of the targets used to test this assay can include cultured cells such as, vascular smooth muscle, endothelial, mesangial, macrophages; or can include tissues such as platelets and aortic segments.

Nitric Oxide Activity Assays

RPPGF (SEQ ID NO:1) and analogue mimetics are tested for their ability to inhibit the generation of nitric oxide using methods described above (FIG. 9). The source of the targets used in this assay can include, but are not limited to, cultured cells such as vascular smooth muscle, endothelial or macrophages; or tissues such as aortic segments.

Cell Proliferation Assays

RPPGF (SEQ ID NO:1) and analogue mimetics are tested for their ability to stimulate proliferation of cultured cells by measuring incorporation of [$^3$H]-thymidine into cellular DNA according to previously published methods (25). Targets for this assay can include, but are not limited to, vascular smooth muscle, endothelial, fibrobalsts or mesangial cells.

Tyrosine Phosphorylation Assays

RPPGF (SEQ ID NO:1) and analogue mimetics are tested for their ability to stimulate tyrosine phosphorylation of cellular proteins using previously published methods (26). Targets for this assay include, but are not limited to, vascular smooth muscle, endothelial, fibroblasts or mesangial cells.

Endotoxin Shock Assays

RPPGF (SEQ ID NO:1) and analogue mimetics are tested for their ability to prolong survival time of animal treated with endotoxin (LPS). These studies are performed as described above for FIGS. 12 and 13. Animals that can be used in these studies include, but are not limited to, rodents, rabbits, pigs or others.

Pharmacological Assays for RPPGF Activity

RPPGF (SEQ ID NO:1) and its analogues are tested for anti-kinin activity in assays in which BK has been shown to have activity including but not limited to:

rat uterus contraction dog saphenous vein contraction rabbit jugular vein contraction guinea pig ilium relaxation ion transport studies in sections of epithelial tissue or cultured cells measuring transport of sodium, chloride, or bicarbonate nitric oxide release from endothelial cells.

These and other systems are described in Hall, Judith M., Bradykinin receptors: Pharmacological properties and biological roles, Pharmac. Therap. 56:131–190, 1992.

Example 3

Screening for Antagonists of RPPGF (SEQ ID NO:1)

Screening for Non-Antibody Antagonists of RPPGF (SEQ ID NO:1)

Compounds are tested for the ability to inhibit the actions of RPPGF (SEQ ID NO:1) by using one or more of the assays described in Example 2 above. Standard pharmacological analysis, such as a Schild analysis (27), of the results from these screening assays are used to determine if the antagonism is competitive or non-competitive in nature.

Screening for Anti-Body Antagonists of RPPGF (SEQ ID NO:1)

Antibodies are raised in rabbits against RPPGF (SEQ ID NO:1) using standard techniques for generation of anti-peptide antibodies. RPPGF-Cysteine coupled to keyhole limpet hemocyanin is used as the immunogen. The obtained antibody is used in standard radioimmunassays which can employ $N^\alpha(^{125}I\text{-des-NH}_2\text{-Tyr})BK1\text{-}5$ or RPPGF-$^{125}I$ as the tracer.

Example 4

Screening for RPPGF Receptors

Identification of a receptor for RPPGF (SEQ ID NO:1) can employ saturation binding isotherms using $N^\alpha(^{125}I\text{-des-NH}_2\text{-Tyr})BK1\text{-}5$ or RPPGF-$^{125}I$ as the radioligand in techniques previously employed and published (25). The target used for these assays can employ cultured cells such as vascular smooth muscle, endothelial, fibroblasts, mesangial, macrophage or tissues such as aorta non-platelets or platelets. These targets can be prepared as whole cells (in suspension or as monolayers), crude homogenates, membranes (crude and solubilized), or cytosolic or nuclear extracts.

Example 5

Radioimmunoassay for RPPGF (SEQ ID NO:1)

Antibodies are raised in rabbits against RPPGF (SEQ ID NO:1) using standard techniques for generation of anti-peptide antibodies. RPPGF-Cysteine coupled to keyhole limpet hemocyanin is used as the immunogen. The obtained antibody is used in standard radioimmunassays which can employ $N^\alpha(^{125}I\text{-des-NH}_2\text{-Tyr})BK1\text{-}5$ or RPPGF-$^{125}I$ (SEQ ID NO:1) as the tracer. Bodily fluids, such as blood, plasma and urine, are prepared for assay as described (28, 29, 30). Plasma samples in population studies are evaluated according to protocols previously described (13, 14).

REFERENCES

1. Cushman, D. W., Cheung, H. S., Sabo, E. F. and Ondetti, M. A.: Design of potent competitive inhibitors of angiotensin-converting enzyme. Carboxyalkanoyl and mercaptoalkanoyl amino acids. Biochemistry 16:5484–5491, 1977.
2. Bhoola, K. D., Figueroa, C. D., and Worthy, K.: Bioregulation of kinins: kallikreins, kininogens, and kininases. Pharmacological Rev. 44: 1–78, 1992.
3. Margolius, H. S.: Kallikreins and kinins: some unanswered questions about system characteristics and roles in human disease. Hypertension 26: 221–229, 1995.
4. Blache, P., Kervan, A., Le-Nguyen, D., and Bataille, D.: Miniglucagon production from glucagon: an extracellular processing of a hormone used as a prohormone. Biochimie 76: 295–299, 1994.
5. Blache, P., Kervan, A., Le-Nguyen, D., Dufour, M., Cohen-Sola, A., Duckworth, W., and Bataille, D.: Endopeptidase from rat liver membranes, which generates miniglucagon from glucagon. J. Biol. Chem. 268: 21748–21753, 1993.
6. Pavoine, C., Brechler, V., Kervan, A., Blache, P., Le-Nguyen, D., Laurent, S., Bataille, D., and Pecker, F.: Miniglucagon<glucagon-(19–29)>is a component of the positive inotropic effect of glucagon. Am. J. Physiol. 260: C993–C999, 1991.
7. Hasan, A. A. K., Amenta, S. and Schmaier, A. H.; Bradykinin and its metabolite, Arg-Pro-Pro-Gly-Phe are selective inhibitors of α-thrombin-induced platelet activation. Circulation 94:517–528, 1996.
8. Greenwood, et al., Multiple display of foreign peptides on a filamentous bacteriophage: Peptides from plasmodium falciparium circumsporozoite protein as antigens. J. Mol. Biol. 206:821–827, 1991.
9. Stewart, J. M.: Bradykinin antagonists: development and applications. Biopolymers (Peptide Science) 37: 143–155, 1995.
10. Majima, M., Shima, C., Saito, M., et al., Postastatin, a novel inhibitor of bradykinin-degrading enzymes in rat urine. European Journal of Pharmacology, 232:181–190, 1993.
11. Shima, C., Majima, M., and Katori, M.: A stable metabolite, Arg-Pro-Pro-Gly-Phe, of bradykinin in the degradation pathway in human plasma. Japan. J. Pharmacol. 60: 111–119, 1992.
12. Margolius, H. S.: Tissue kallikreins and kinins: regulation and roles in hypertensive and diabetic diseases. Annu. Rev. Pharmacol. 29: 343–364, 1989.
13. Zinner, S. H., Margolius, H. S., Rosner, B., Keiser, H. R., and Kass, E. H.: Familial aggregation of urinary kallikrein concentration in childhood. Am. J. Epidemiol. 104: 124–132, 1976.

14. Zinner, S. H., Margolius, H. S., Rosner, B., and Kass, E. H.: Stability of blood pressure rank and urinary kallikrein in childhood. Circulation 58: 908–915, 1978.
15. Privitera, P. J. and Yates, P.: Hypertensive effect of tissue kallikrein in rostral ventroloateral medulla is mediated by brain kinis. Brain Research 704:103–106, 1995.
16. Privitera, P. J., Thibodeaux, H. and Yates, P.; Rostral ventrolateral medulla as a site for the central hypertensive action of kinins. Hypertension 23:52–58, 1994.
17. Privitera, P. J., Granata, A. R., Underwood, M. D., Gaffney, T. E. and Reis, D. J.: C1 area of the Rostral Ventrolateral Medulla as a site for the central hypotensive action of propranolol. Journal of Pharmacology and Experimental Therapeutics 246:529–533, 1988.
18. Nishimiya, T., Daniel, H. B., Webb, J. G., Oatis, J., Walle, T., Gaffney, T. E. and Halsuhka, P. V.: Journal of Pharmacology and Experimental Therapeutics, 253:207–213, 1990.
19. Brizzolara-Gourdie, A. and Webb, J. G.; Angiotensin II potentiates vasocilation of rat aorta by cAMP elevating agonists. Journal of Pharmacology and Experimental therapeutics 281:354–359, 1997.
20. Miller, L. J., Rosenzweig, S. A. and Jamieson, J. D.; Preparation and characterization of a probe for the cholecystokinin octapeptide receptor, $N^{\alpha}(^{125}I$-desaminotyrosyl)CCK-8, and its interactions withpancreatic acini. Journal of Biological Chemistry, 256(23):12417–12423, 1981.
21. Morinelli, t. A., Mais, D. E., Oatis, J. E., Crumbley, A. J. and Halushka, P. V.: Characterization of thromboxane A2/prostaglandin H2 receptors in human vascular smooth muscle cells. Life Sciences, 46:1765–1772, 1990.
22. Morinelli, T. A., Oatis, J. E., Okwu, A. K., Mais, D. E., Mayeux, P. R., Masuda A., Knapp, D. R. and Halushka, P. V.; Characterization of an $^{125}I$-labeled thromboxane A2/prostaglandin H2 receptor agonists. Journal of Pharmacology and Experimental Therapeutics, 251:557–562, 1989.
23. Zhang, J., Sata, M., Duzic, E., Kubalak, S. W., Lanier, S. M. and Webb, J. G.; Adenylyl cyclaase isoforms and vasopressin enhancement of agonist-stimulated cAMP in vascular smooth muscle cells. American Journal of Physiology 273 (Heart Circ. Physiol. 42):H971–980, 1997.
24. Morinelli, T. A., Tempel, G. E., Jaffa, A. A., Silva, R. H., Naka, M., Folger, W. and Halushka, P. V.: Thromboxane A2/prostaglandin H2 receptors in streptozotocin-induced diabetes: Effects of insulin therapy in the rat. Prostaglandins 45:427–438, 1993.
25. Morinelli, T. A., Zhang, L. M., Neman, W. H. and Meier, K. E., Thromboxane A2/prostaglandin H2-stimulated mitogenesis of coronary artery smooth muscle cells involves activation of mitogen-activated protein kinase and S6 kinase. Journal of Biological Chemistry, 269(8):5693–5698, 1994.
26. Morinelli, T. A., Finley, E. L., Jaffa, A. A., Kurtz, D. T. and Ullian, M. E.; Tyrosine phosphorylation of phosphatidylinositol 3-Kinase and of the thromboxane A2 (TXA2) receptors by the TXA2 mimetic I-BOP in A7r5 cells. biochemical Pharmacology 53:1823–1832, 1997.
27. Schild, H. O.; Drug antagonism and pAx. Pharmacologica Reviews 9;242–246, 1957.
28. Majima, M., Sunahara, N., Harada, Y., and Katori, M.: Detection of the degradation products of bradykinin by enzyme immunoassays as markers for the release of kinin in vivo. Biochem. Pharmacol. 45: 559–567, 1993.
29. Markit-M [1–5] Bradykinin Kit. Dainippon Pharmaceutical Co., Ltd., Osaka, 541 Japan.
30. Campbell D., Kladis, S. and Duncan, A.; Hypertension 21:155–165, 1993.
31. Erdos, E. G., and Skidgel, R. A.: Neutral endopeptidase 24.11 (enkephalinase) and related regulators of peptide hormones. FASEB J. 3:145–151, 1989.
32. Ura, N., Carretero, O. A., Erdos, E. G.: Role of endopeptidase 24.11 in kinin metabolism in vitro and in vivo. Kidney Int. 32:507–513, 1987.
33. Trippodo, N. C., Balkrushina, C., and Fox, M.: Repression of angiotensin II and potentiation of bradykinin contribute to the synergistic effects of dual metalloprotease inhibition in heart failure. J. Pharmacol. Exp. Therap. 272: 619–627, 1995.
34. Trippodo, N. C., Robl, J. A., Asaad, M. M., Bird, J. E., Panchal, B. C., Schaeffer, T. R., Fox, M., Giancarli, M. R., and Cheung, H. S.: Cardiovascular effects of the novel dual inhibitor of neutral endopeptidase and angiotensin-converting enzyme BMS-182657 in experimental hypertension and heart failure. J. Pharmacol. Exp. Therap. 275:745–752, 1995.
35. Favrat, B., Burnier, M., Nussberger, J., Lecomte, J. M., Brouard, R., Waeber, B., and Brunner, H. R.: Neutral endopeptidase versus angiotensin converting enzyme inhibition in essential hypertension. J. Hypertension 13: 797–804, 1995.
36. Chakir, M., D'Orleans-Juste, P., Plante, G. E.: Neutral endopeptidase inhibition, a new approach in the exploration of diabetic vasculopathy in rats. Eur. J. Pharmacol. 285: 11–18, 1995.
37. Lerner, U. H., Jones, I. L., and Gustafson, G. T.: Bradykinin, a new potential mediator of inflammation-induced bone resorption. Arthritis and Rheumatism. 30:530–540, 1987.
38. Lerner, U. H.: Bradykinin synergistically potentiates interleukin-1 induced bone resorption and prostanoid biosynthesis in neonatal mouse calvarial bones. Biochem. Biophys. Res. Comm. 175: 775–783, 1991.
39. Gaginella, T. S. and Kachur, J. F.: Kinins as mediators of intestinal secretion. Am. J. Physiol. 256: G1–G15, 1989.
40. Smith, G. P., 1985. Filamentous fusion phage: novel expression vectors that display cloned antigens on the virion surface. Science, 228(4705): 1315-7.
41. Cwirla, S. E., et al., 1990. Peptides on phage: a vast library of peptides for identifying ligands. *Proc Natl Acad Sci USA*, 1990. 87(16): 6378–82.
42. Scott, J. K. and G. Smith, 1990. Searching for peptide ligands with an epitope library. *Science,* 249(4967): 386–90.
43. Kay, B. K., Adey, N. B., He, Y. S., Manfredi, J. P., Mataragnon, A. H., and Fowlkes, D. M. (1993). An M13 phage library displaying random 38-amino-acid peptides as a source of novel sequences with affinity to selected targets. Gene 128, 59–65.
44. Devlin, J. J., L. C. Panganiban, and P. E. Devlin. 1990. Random peptide libraries: a source of specific protein binding molecules. Science, 249(4967): 404–6.
45. Dedman, J. R., Kaetzel, M. A., Chan, H. C., Nelson, D. J., and Jamieson, G., Jr. (1993). Selection of targeted biological modifiers from a bacteriophage library of random peptides. The identification of novel calmodulin regulatory peptides. J Biol Chem 268, 23025–30.
46. Sparks, A. B., Quilliam, L. A., Thorn, J. M., Der, C. J., and Kay, B. K. (1994). Identification and characterization of Src SH3 ligands from phage-displayed random peptide libraries. J Biol Chem 269, 23853–6.
47. Blond-Elguindi, S., Cwirla, S. E., Dower, W. J., Lipshutz, R. J., Sprang, S. R., Sambrook, J. F., and Gething, M. J. (1993). Affinity panning of a library of peptides displayed on bacteriophages reveals the binding specificity of BiP. Cell 75, 717–28.

What is claimed is:

1. A method of screening for a mimetic of RPPGF (SEQ ID NO:1) comprising:

a) contacting a model system known to express an activity of RPPGF (SEQ ID NO:1) in the presence of RPPGF (SEQ ID NO:1) with a putative mimetic in the absence of RPPGF (SEQ ID NO:1);

b) detecting the presence or absence of the known activity of RPPGF (SEQ ID NO:1) in the presence of the putative mimetic; and c) correlating the presence of the activity with the presence of a mimetic of RPPGF (SEQ ID NO:1).

2. The method of claim 1, wherein the activity is an activity contrary to an activity of bradykinin.

3. The method of claim 1, wherein the activity is an anti-hypotensive activity, associated with hypotension.

4. The method of claim 1, wherein the activity is an anti-endotoxemic activity, associated with endotoxemia secondary to bacterial sepsis.

5. The method of claim 1, wherein the activity is an anti-diuretic activity, associated with electrolyte and water excretion.

6. The method of claim 1, wherein the activity is an increase in intracellular calcium.

7. The method of claim 1, wherein the activity is an increase in DNA synthesis.

8. The method of claim 1, wherein the activity is an increase in tyrosyl phosphorylation of cytoplasmic proteins.

9. The method of claim 1, wherein the activity is an increase in prostaglandin synthesis.

10. The method of claim 1, wherein the activity is an increase in cyclooxygenase products.

11. The method of claim 1, wherein the activity is inhibition of inducible nitric oxide synthase.

* * * * *

UNITED STATES PATENT AND TRADEMARK OFFICE
Certificate

Patent No. 6,071,710                                        Patented: June 6, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Harry S. Margolius, Mt. Pleasant, SC; Philip J. Privitera, Charleston, SC; Ayad A. Jaffa, Mt. Pleasant, SC; Jerry G. Webb, Charleston, SC; and Thomas A. Morinelli, Charleston, SC.

Signed and Sealed this Thirteenth Day of January 2004.

*YVONNE EYLER*
*Supervisory Patent Examiner*
*Art Unit 1646*

SEQUENCE LISTING

<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 1

Arg Pro Pro Gly Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 2

Phe Gly Pro Pro Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 3

Arg Pro Pro Gly Phe Ser Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 4

Pro Pro Gly Phe Ser Pro
1               5

<210> SEQ ID NO 5
<211> LENGTH: 17
<212> TYPE: PRT
<213> ORGANISM: Artificial Sequence
<220> FEATURE:
<223> OTHER INFORMATION: NOTE: Xaa can be any amino acid and some or all of the amino acids designated Xaa may not be present
<220> FEATURE:
<223> OTHER INFORMATION: Description of Artificial Sequence:/Note = synthetic construct

<400> SEQUENCE: 5

Xaa Xaa Xaa Xaa Xaa Xaa Arg Pro Pro Gly Phe Xaa Xaa Xaa Xaa Xaa Xaa
1               5                   10                  15

<210> SEQ ID NO 6

```
<211> LENGTH: 16
<212> TYPE: PRT
<213> ORGANISM: Artificial Sequence
<220> FEATURE:
<223> OTHER INFORMATION: NOTE: Xaa can be any amino acid and some or all
      of the amino acids designated Xaa may not be present
<220> FEATURE:
<223> OTHER INFORMATION: Description of Artificial Sequence:/Note =
      synthetic construct

<400> SEQUENCE: 6

Xaa Xaa Xaa Xaa Xaa Xaa Pro Pro Gly Phe Xaa Xaa Xaa Xaa Xaa Xaa
 1               5                  10                  15

<210> SEQ ID NO 7
<211> LENGTH: 17
<212> TYPE: PRT
<213> ORGANISM: Artificial Sequence
<220> FEATURE:
<223> OTHER INFORMATION: NOTE: Xaa can be any amino acid and some or all
      of the amino acids designated Xaa may not be present
<220> FEATURE:
<223> OTHER INFORMATION: Description of Artificial Sequence:/Note =
      synthetic construct

<400> SEQUENCE: 7

Xaa Xaa Xaa Xaa Xaa Xaa Phe Gly Pro Pro Arg Xaa Xaa Xaa Xaa Xaa Xaa
 1               5                  10                  15

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 8

Pro Pro Gly Phe
 1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 9

Pro Pro Gly Arg Ser Pro
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 10

Lys Arg Pro Pro Gly Phe
 1               5

<210> SEQ ID NO 11
<211> LENGTH: 3
<212> TYPE: PRT
<213> ORGANISM: Artificial Sequence
```

-continued

```
<220> FEATURE:
<223> OTHER INFORMATION: Description of Artificial Sequence:/Note =
      synthetic construct

<400> SEQUENCE: 11

Arg Pro Pro
1

<210> SEQ ID NO 12
<211> LENGTH: 15
<212> TYPE: PRT
<213> ORGANISM: Artificial Sequence
<220> FEATURE:
<223> OTHER INFORMATION: NOTE: Xaa can be any amino acid and some or all
      of the amino acids designated Xaa may not be present
<220> FEATURE:
<223> OTHER INFORMATION: Description of Artificial Sequence:/Note =
      synthetic construct

<400> SEQUENCE: 12

Xaa Xaa Xaa Xaa Xaa Xaa Arg Pro Pro Xaa Xaa Xaa Xaa Xaa Xaa
1               5                   10                  15

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 13

His Pro Pro Gly Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 14

Arg Pro Pro Ala Phe
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 15

Pro Arg Gly Phe Pro
1               5
```